United States Patent
Ueda et al.

(10) Patent No.: US 10,661,069 B2
(45) Date of Patent: May 26, 2020

(54) CONNECTOR AND INFUSION SET

(71) Applicant: TERUMO KABUSHIKI KAISHA, Tokyo (JP)

(72) Inventors: Yashuhiro Ueda, Kofu (JP); Toshihiko Kakinoki, Yamanashi (JP); Ryouhei Fujieda, Laguna (PH)

(73) Assignee: TERUMO KABUSHIKI KAISHA, Tokyo (JP)

( * ) Notice: Subject to any disclaimer, the term of this patent is extended or adjusted under 35 U.S.C. 154(b) by 55 days.

(21) Appl. No.: 15/277,686

(22) Filed: Sep. 27, 2016

(65) Prior Publication Data

US 2017/0014614 A1    Jan. 19, 2017

Related U.S. Application Data

(63) Continuation of application No. PCT/JP2015/000476, filed on Feb. 3, 2015.

(30) Foreign Application Priority Data

Mar. 28, 2014   (JP) .................................. 2014-067721

(51) Int. Cl.
*A61M 39/26*   (2006.01)
*A61M 39/10*   (2006.01)
(Continued)

(52) U.S. Cl.
CPC ........ *A61M 39/10* (2013.01); *A61M 5/16813* (2013.01); *A61M 39/045* (2013.01);
(Continued)

(58) Field of Classification Search
CPC .... A61M 39/10; A61M 39/045; A61M 39/26; A61M 2039/0063; A61M 2039/0072; A61M 2206/20; A61M 5/16813
See application file for complete search history.

(56) References Cited

U.S. PATENT DOCUMENTS 5,199,948 A  *  4/1993  McPhee  .............. A61M 39/045
                                              604/167.02
5,360,413 A  *  11/1994  Leason  ................. A61M 39/26
                                              137/843
(Continued)

FOREIGN PATENT DOCUMENTS

CN      203763665 U  *  8/2014  ............ A61M 39/10
JP      2010-514528 A     5/2010
(Continued)

OTHER PUBLICATIONS

CN Office Action for Appl. Ser. No. 201580016646.1, 11 pages.
(Continued)

*Primary Examiner* — William R Carpenter
*Assistant Examiner* — Tezita Z Watts
(74) *Attorney, Agent, or Firm* — Foley & Lardner LLP

(57) ABSTRACT

A connector includes an elastic valve body that includes a top face on which a slit is formed and a bottom face opposite the top face; and a holding section that is in contact with the top face and the bottom face of the elastic valve body and holds the elastic valve body. The holding section surrounds the slit, and the elastic valve body includes a peripheral section that is positioned outward of a portion of the elastic valve body that is held by the holding section. The elastic valve body and the holding section are configured such that a volume of the peripheral section in a state in which the elastic valve body is held by the holding section is larger than a volume of the peripheral section in a state in which the elastic valve body is not held by the holding section.

12 Claims, 15 Drawing Sheets

(51) Int. Cl.
*A61M 39/04* (2006.01)
*A61M 5/168* (2006.01)
*A61M 39/00* (2006.01)

(52) U.S. Cl.
CPC ..... *A61M 39/26* (2013.01); *A61M 2039/0063* (2013.01); *A61M 2039/0072* (2013.01); *A61M 2206/20* (2013.01)

(56) References Cited

U.S. PATENT DOCUMENTS

2006/0184140 A1    8/2006    Okiyama
2008/0108939 A1    5/2008    Moulton
2010/0030163 A1    2/2010    Carrez et al.
2011/0160679 A1    6/2011    Okiyama et al.

FOREIGN PATENT DOCUMENTS

| | | | |
|---|---|---|---|
| JP | 2010-148757 A | 7/2010 | |
| JP | WO 2012133131 A1 * | 10/2012 | .......... A61M 39/045 |
| JP | 2014-000459 A | 1/2014 | |
| JP | 2014-028285 A | 2/2014 | |
| WO | WO-2011/064738 A2 | 6/2011 | |
| WO | WO-2012133131 A1 * | 10/2012 | .......... A61M 39/045 |

OTHER PUBLICATIONS

Extended European Search Report dated Aug. 30, 2017 in corresponding application 15770150.9.
International Search Report issued in International Patent Application No. PCT/JP2015/000476 dated May 12, 2015.

* cited by examiner

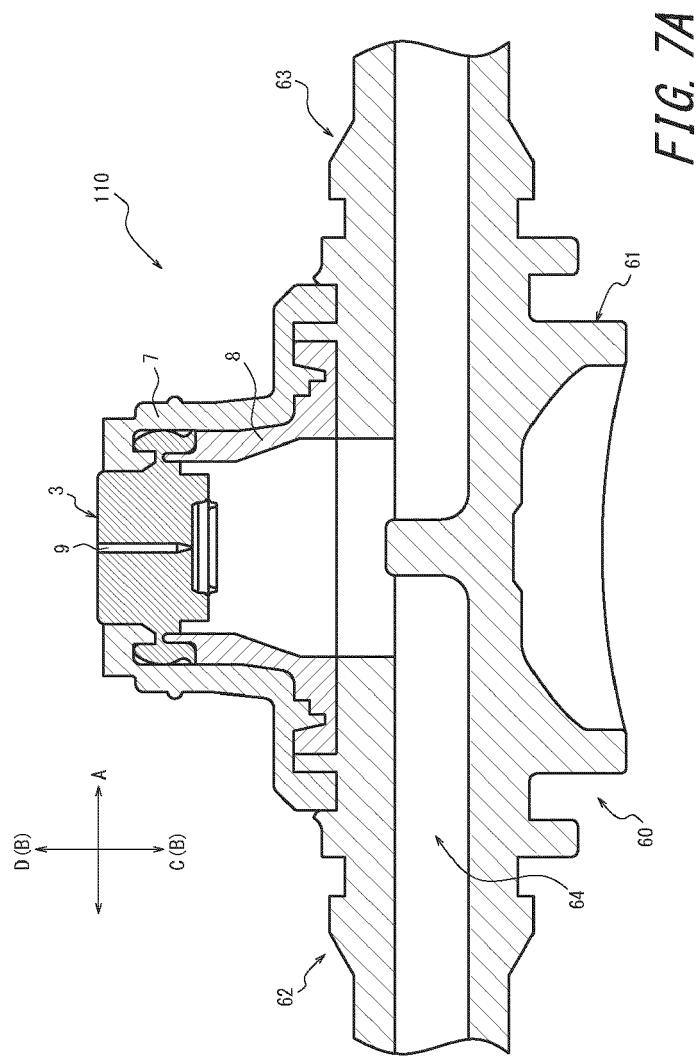

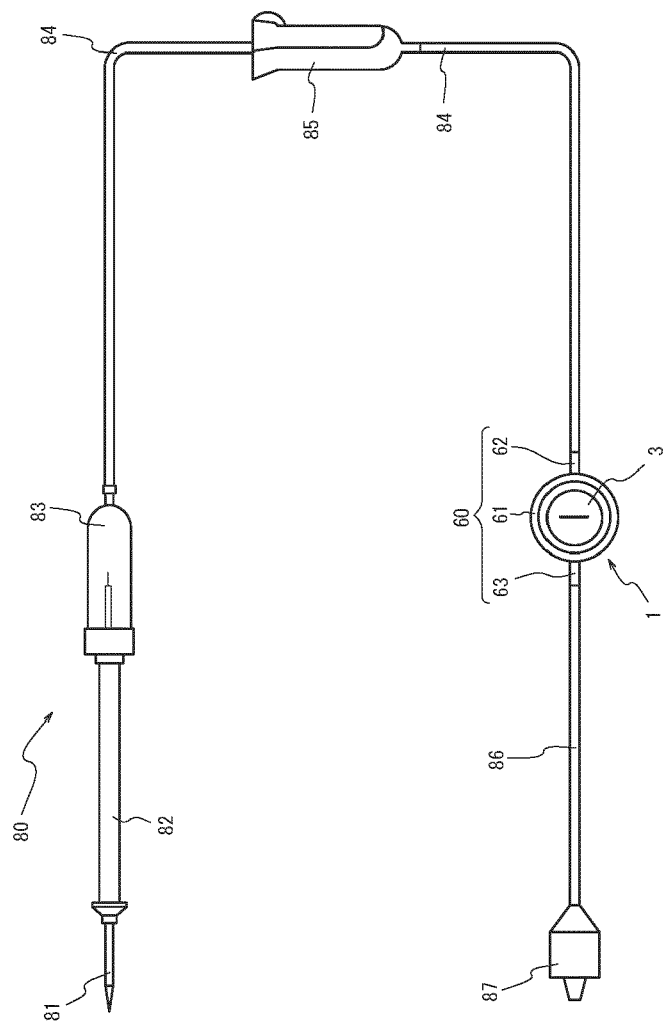

CONNECTOR AND INFUSION SET

CROSS-REFERENCE TO RELATED APPLICATIONS

The present application is a bypass continuation of PCT Application No. PCT/JP2015/000476, filed on Feb. 3, 2015, which claims priority to Japanese Application No. 2014-067721, filed on Mar. 28, 2014. The disclosures of these applications are hereby incorporated by reference in their entireties.

BACKGROUND

The present disclosure relates to a connector and an infusion set, and particularly to a connector that is capable of connecting thereto a male connector such as various medical devices and an infusion set provided with the connector.

BACKGROUND ART

Conventionally, when infusion, blood transfusion, or artificial dialysis is performed, liquid is fed into the body using a medical tube. When another liquid such as a liquid medicine is joined to the liquid inside the tube, a connector that is capable of liquid-tightly connecting a male connector such as a syringe and a luer taper member to the medical tube is used. A male connector such as a syringe and a luer taper member may be called a male luer, and a connector connected to the male luer may be called a female luer.

Such a connector capable of connecting a male connector is disclosed, for example, in JP 2010-148757 A. A medical connector disclosed in JP 2010-148757 A is provided with a mixed injection port which causes an engaging projection of an annular ring and an engaging projection part of a cylindrical port to enter annular grooves provided, respectively, on an outer surface and an inner surface of a valve member so as to support the valve member in a sandwich state, in which an annular fixing section of the valve member is held and assembled by the annular ring and the cylindrical port.

SUMMARY

The mixed injection port of JP 2010-148757 A is provided with an annular fitting concave groove, which extends over the entire periphery of an inner peripheral face of a small diameter cylinder portion of the cylindrical port in the circumferential direction, and the annular fixing section of the valve member abuts on the entire inner surface of the fitting concave groove in an intimate-contact state so as to prevent formation of a gap in the fitting concave groove.

A depth dimension of the fitting concave groove is a projecting height dimension of the above-described engaging projection part, and is set to be equal to or slightly larger than a depth dimension of the annular groove of the valve member. In addition, a groove width dimension of the fitting concave groove in a radial direction is set to be equal to or slightly smaller than a width dimension of a part projecting toward the inner surface than a constricted-shaped part of the annular fixing section of the valve member. Apart of the annular fixing section of the valve member on the outer surface side, and the engaging projection of the annular ring have the similar dimensional relationship.

That is, a space, which is defined by the cylindrical port and the annular ring and configured to house the annular fixing section of the valve member, has a sectional shape which matches with a sectional shape of the annular fixing section in the single valve member that is not assembled in the mixed injection port, or a sectional shape that prevent the annular fixing section from being housed unless holding and compressing the annular fixing section in the thickness direction and the radial direction in JP 2010-148757 A.

However, the connector provided with the mixed injection port of JP 2010-148757 A has a problem that a part of the valve member is pushed inward in the radial direction from a part compressed by the engaging projection of the annular ring and the engaging projection part of the cylindrical port when the valve member as an elastic valve body is held and compressed, and a central section of the valve member becomes slack.

When opening and closing operations of the elastic valve body are repeatedly performed by insertion and removal of the male connector in the slack state of the central section of the elastic valve body, the elastic valve body is moved from an originally fixed position, and there is a risk that it is hard to restore the original position even after removing the male connector.

In view of the above problem, an object of certain embodiments of the present invention is to provide a connector and an infusion set capable of suppressing generation of slack in a central section of an elastic valve body.

In a first embodiment, a connector includes: an elastic valve body which includes a top face on which a slit is formed and a bottom face on an opposite side of the top face; and a holding section which is in contact with the top face and the bottom face of the elastic valve body and holds the elastic valve body, the holding section is provided to surround the slit, and the elastic valve body includes a peripheral section which is positioned on an outer side of a position thereof being held by the holding section when the elastic valve body is viewed from the top face side, and a volume of the peripheral section in a state in which the elastic valve body is held by the holding section is larger than a volume of the peripheral section in a state in which the elastic valve body is not held by the holding section.

In one aspect, the elastic valve body has a substantially circular outer shape when viewed from the top face side, a housing which includes an inner wall section that surrounds a perimeter of the elastic valve body in a radial direction of the elastic valve body on an outer side, in the radial direction, of the peripheral section is further provided, and a gap is provided between the peripheral section and the inner wall section in the state in which the elastic valve body is held by the holding section.

In one aspect, the elastic valve body has a substantially circular outer shape when viewed from the top face side. A housing which includes an inner wall section that surrounds a perimeter of the elastic valve body in a radial direction of the elastic valve body on an outer side, in the radial direction, of the peripheral section is further provide. The entire peripheral section and the inner wall section are in contact with each other in the state in which the elastic valve body is held by the holding section.

In one aspect, the elastic valve body includes a constricted section which is held by the holding section, and an inner diameter of the inner wall section becomes maximum at a position on an outer side, in the radial direction, with respect to the constricted section in a cross-section parallel to a thickness direction, perpendicular to the radial direction, of the elastic valve body.

In one aspect, the inner wall section has a curved shape projecting outward in the radial direction such that the inner diameter becomes maximum at the position on the outer side, in the radial direction, with respect to the constricted section in the cross-section parallel to the thickness direction.

In one aspect, the holding section is provided in the housing, the holding section is provided with an annular top-face-side holding section, which is in contact with the top face of the elastic valve body, and an annular bottom-face-side holding section which is in contact with the bottom face and holds the elastic valve body together with the top-face-side holding section, the peripheral section is housed in a housing space which is defined by the inner wall section, the top-face-side holding section, the bottom-face-side holding section, a top-face-side coupling section which connects an end of the inner wall section and the top-face-side holding section, and a bottom-face-side coupling section which connects another end of the inner wall section and the bottom-face-side holding section, in a cross-section perpendicular to the radial direction, and a gap is provided between the peripheral section and the top-face-side coupling section and/or the bottom-face-side coupling section in the state in which the elastic valve body is held by the holding section.

In one aspect, the holding section is provided in the housing, the holding section is provided with an annular top-face-side holding section, which is in contact with the top face of the elastic valve body, and an annular bottom-face-side holding section which is in contact with the bottom face and holds the elastic valve body together with the top-face-side holding section, the peripheral section is housed in a housing space which is defined by the inner wall section, the top-face-side holding section, the bottom-face-side holding section, a top-face-side coupling section which connects an end of the inner wall section and the top-face-side holding section, and a bottom-face-side coupling section which connects another end of the inner wall section and the bottom-face-side holding section, in a cross-section perpendicular to the radial direction, and the peripheral section and the entire top-face-side coupling section and/or the entire bottom-face-side coupling section are in contact with each other in the state in which the elastic valve body is held by the holding section.

In another embodiment, a connector includes: an elastic valve body which includes a top face on which a slit is formed and a bottom face on an opposite side of the top face and has a substantially circular outer shape when viewed from the top face side; and a housing which includes a holding section that is in contact with the top face and the bottom face of the elastic valve body to surround the slit when the elastic valve body is viewed from the top face side and holds the elastic valve body, the housing includes an inner wall section that surrounds a perimeter of the elastic valve body in a radial direction of the elastic valve body on an outer side, in the radial direction, of the holding section, and a maximum inner diameter of the inner wall section is larger than a maximum outer diameter of the elastic valve body in a state in which the elastic valve body is not held by the holding section.

In one aspect, the maximum inner diameter of the inner wall section is larger than a maximum outer diameter of the elastic valve body in a state in which the elastic valve body is held by the holding section.

In one aspect, the inner wall section is in contact with an outer wall of the elastic valve body so that the maximum inner diameter of the inner wall section and the maximum outer diameter of the elastic valve body become equal in the state in which the elastic valve body is held by the holding section.

A third aspect of the present invention is an infusion set provided with the connector.

According to a connector and an infusion set of certain embodiments of the present invention, it is possible to suppress generation of slack in a central section of an elastic valve body.

BRIEF DESCRIPTION OF THE DRAWINGS

FIG. 7A is a sectional view illustrating a connector provided with a holder which has a different shape from a holder of FIG. 1 or 6 among holders that can be applied to the present invention.

FIG. 13 is a diagram illustrating an infusion set as an embodiment of the present invention.

DETAILED DESCRIPTION

Hereinbelow, embodiments of a connector and an infusion set according to the present invention will be described with reference to FIGS. 1 to 14B. Common members are denoted by identical reference signs throughout the drawings.

Figure 1:
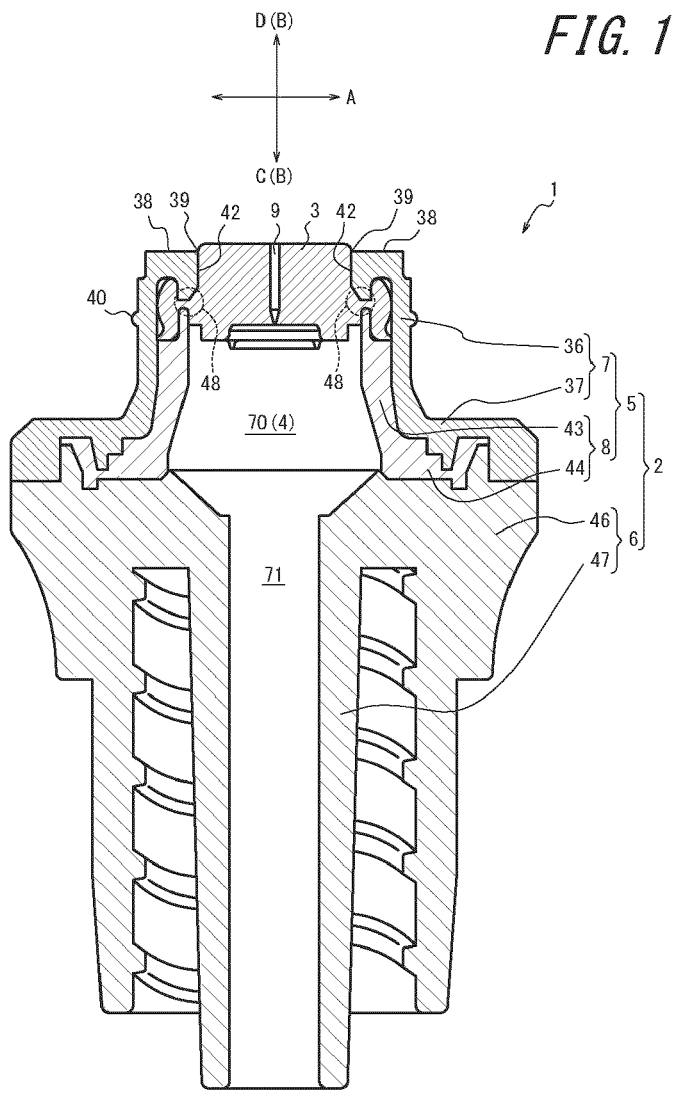
FIG. 1 illustrates a sectional view of a connector 1 as an embodiment of the present invention.

First, one embodiment of the connector according to the present invention will be described. FIG. 1 is a sectional view of a connector 1 as the present embodiment.

As illustrated in FIG. 1, the connector 1 is provided with a housing 2 and an elastic valve body 3 which is attached to the housing 2.

The housing 2 is configured to include a cap 5, which defines an insertion port 4 into which a male connector 100 (refer to FIG. 12) is inserted from the outside, and a holder 6 which supports the cap 5. A hollow section 70 defined by the cap 5 corresponds to the insertion port 4 in the present embodiment.

The cap 5 includes a top face cap 7 and a bottom face cap 8, and the elastic valve body 3 (described below) is compressed and held by the top face cap 7 and the bottom face cap 8, and fixedly positioned inside the hollow section 70. The hollow section 70 serving as the insertion port 4 described above is defined by the top face cap 7 and the bottom face cap 8 in the present embodiment.

The holder 6 is a member that supports the top face cap 7 and the bottom face cap 8. Both the top face cap 7 and the bottom face cap 8 are configured to be supported by the holder 6 in a contact manner in the present embodiment, but a configuration in which the bottom face cap 8 is held by the top face cap 7, and only the top face cap 7 is brought into contact with the holder 6 so as to be supported by the holder 6 may be employed. On the contrary, it may be configured such that the top face cap 7 is held by the bottom face cap 8, and only the bottom face cap 8 is brought into contact with the holder 6 so as to be supported by the holder 6.

Examples of materials for the holder 6 and the top face cap 7 and the bottom face cap 8, serving as the cap 5, which form the housing 2, include various resin materials such as polyolefin such as polyethylene, polypropylene, and an ethylene-propylene copolymer; an ethylene-vinyl acetate copolymer (EVA); polyvinyl chloride; polyvinylidene chloride; polystyrene; polyamide; polyimide; polyamide-imide; polycarbonate; poly(4-methylpentene-1); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride and other fluororesins. In addition, a blend or a polymer alloy containing one or more kinds of the above materials may also be used. Alternatively, various glass materials, ceramic materials, or metal materials may be used.

The elastic valve body 3 has a slit 9 so that the elastic valve body 3 elastically deforms to open or close the slit 9 when the male connector 100 (refer to FIG. 12) is attached to or detached from the connector 1, and the slit 9 is arranged so as to close the insertion port 4 which is defined by the top face cap 7 and the bottom face cap 8 serving as the cap 5. Specifically, the elastic valve body 3 is held by a holding section 48 (refer to FIG. 6), configured of the top face cap 7 and the bottom face cap 8, and a position thereof is fixed inside the connector 1.

The elastic valve body 3 is molded and formed to be elastically deformable. Examples of the material of the elastic valve body 3 include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer, and a material mixed with one or two or more kinds of these materials may be used.

In addition, the hardness of the elastic valve body 3 is preferably 20 to 60° (A hardness). Accordingly, it is possible to ensure a moderate elastic force in the elastic valve body 3, and thus, elastic deformation (described below) can be generated in the elastic valve body 3.

Hereinbelow, each member and a characteristic part constituted by each member in the present embodiment will be described in detail.

[Elastic Valve Body 3]

Figure 2:
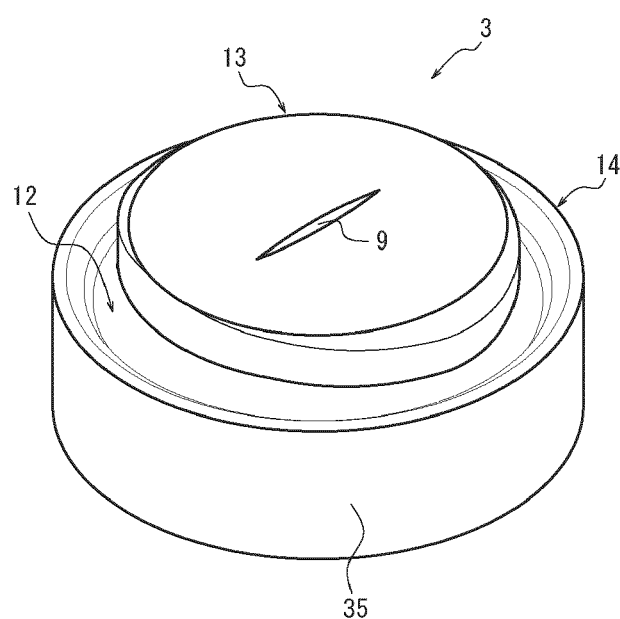
FIG. 2 is a perspective view of an elastic valve body alone which is used in the connector 1.
Figure 3A:
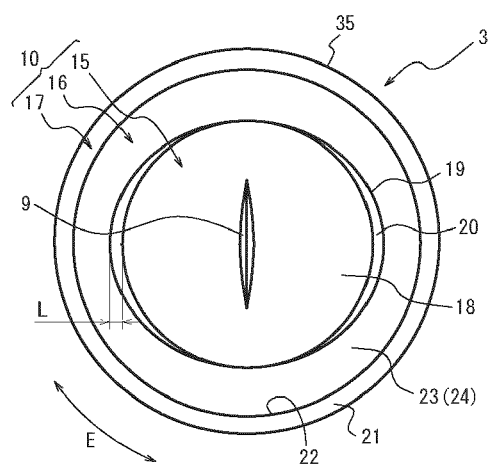
FIG. 3A illustrates a top surface of the elastic valve body of FIG. 2.
Figure 3B:
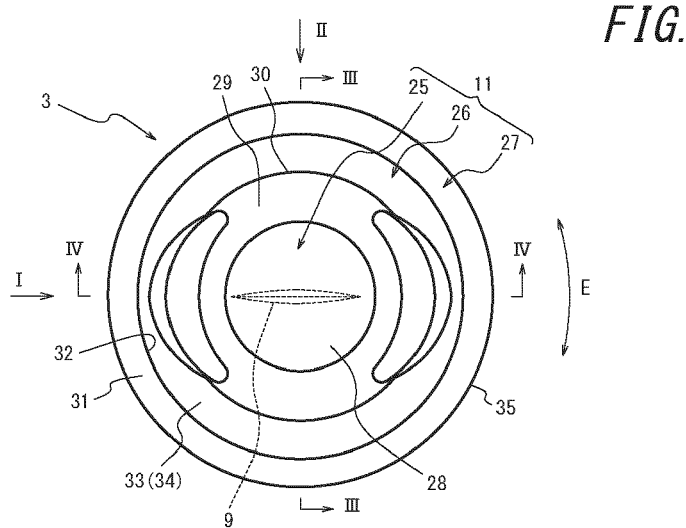
FIG. 3B illustrates a bottom face thereof.
Figure 4A:
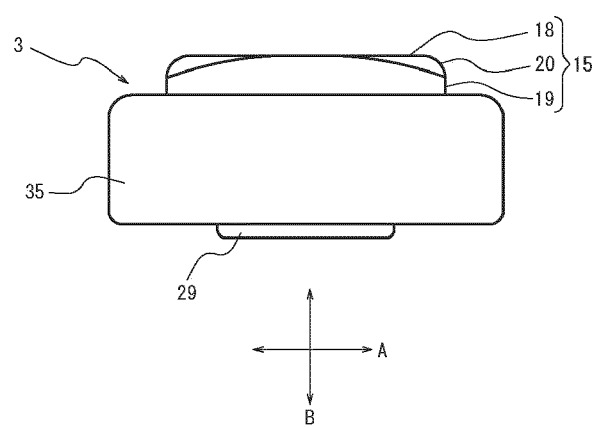
FIG. 4A illustrates a side view of the elastic valve body viewed from a direction I of FIG. 3B.
Figure 4B:
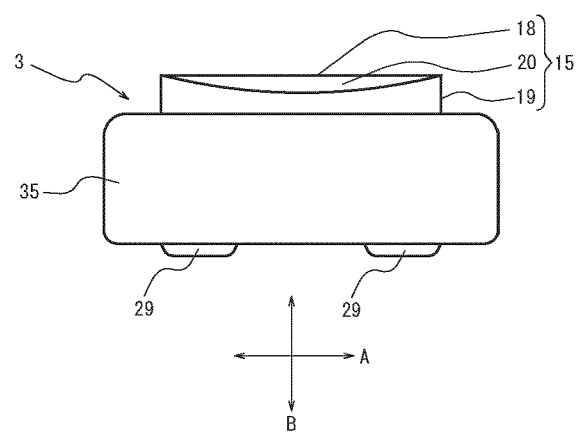
FIG. 4B illustrates a side view viewed from a direction II of FIG. 3B.

FIG. 2 is a perspective view of the elastic valve body 3 alone. FIG. 3A and FIG. 3B are diagrams illustrating a top face 10 and a bottom face 11 of the elastic valve body 3 alone, respectively, and FIG. 4A and FIG. 4B illustrate side views of the elastic valve body 3 viewed from directions I and II, respectively, illustrated in FIG. 3B. In addition, FIG. 5A and FIG. 5B are diagrams illustrating sectional views taken along lines III-III and IV-IV, respectively, of the elastic valve body 3 in FIG. 3B.

Figure 5A:
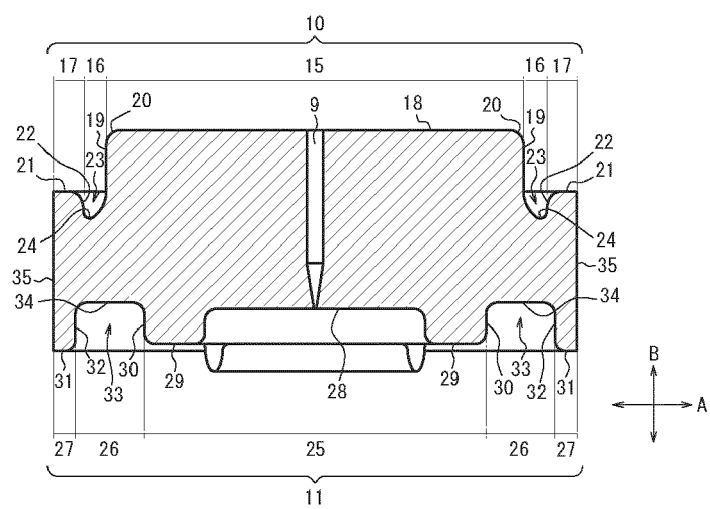
FIG. 5A illustrates a sectional view of the elastic valve body taken along line III-III of FIG. 3B.
Figure 5B:
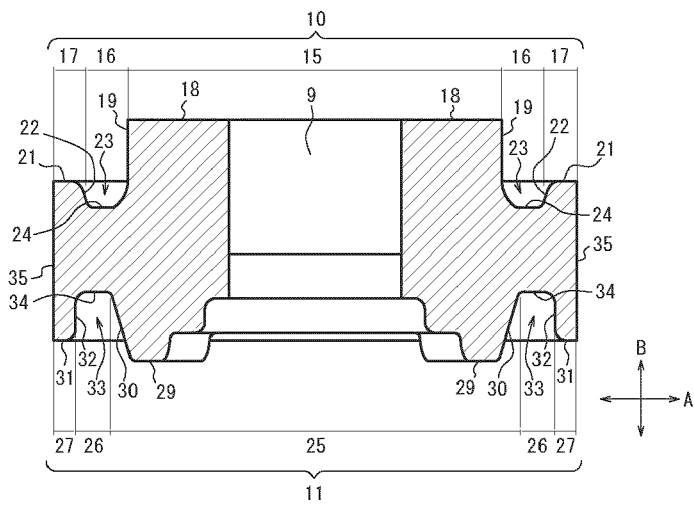
FIG. 5B illustrates a sectional view taken along line IV-IV of FIG. 3B.

As illustrated in FIGS. 2 to 5B, the elastic valve body 3 is a disc-like valve body which has a substantially circular outer shape when viewed from the top face 10 side, and the elastic valve body 3 is provided with a constricted section 12 which is held by the holding section 48 (described below) (refer to FIG. 6) of the housing 2 in a radial direction A of the elastic valve body 3, a central section 13 which is positioned on an inner side than a position of being held by the holding section 48 in the radial direction A, and a peripheral section 14 which is positioned on an outer side of the position of being held by the holding section 48 in the radial direction A as illustrated in FIGS. 5A and 5B.

The top face 10, which is a part of an outer wall of the elastic valve body 3, is configured of a central top face region 15 of the central section 13, a constricted section top face region 16 of the constricted section 12, which is positioned on the outer side of the central top face region 15 in the radial direction A, and a peripheral section top face region 17 of the peripheral section 14 which is positioned on the further outer side of the constricted section top face region 15 in the radial direction A.

As illustrated in FIGS. 2 to 5B, the central top face region 15 has a planar central flat face 18, which extends in the radial direction A on the outer side (upper side in FIGS. 4A to 5B) of the constricted section top face region 16 and the peripheral section top face region 17, and an annular side wall section 19 which extends in a thickness direction B (direction perpendicular to the radial direction A) perpendicular to the central flat face 18.

The straight slit 9 is formed on the center of the central flat face 18. The slit 9 is molded, and does not penetrate the elastic valve body 3 up to the bottom face 11 when molded, and penetrates the elastic valve body 3 up to the bottom face 11 when, for example, the male connector 100 is first inserted after the molding. A process of allowing the slit 9 to penetrate the elastic valve body 3 may be executed as a part of the manufacturing process after the molding is completed.

As illustrated in FIG. 3A, the central flat face 18 of the central top face region 15 is formed in an elliptical shape having a minor axis in a longitudinal direction (vertical direction in FIG. 3A) of the slit 9 and a major axis in a direction (lateral direction in FIG. 3A) perpendicular to the longitudinal direction of the slit 9 in a state in which the elastic valve body 3 is not housed in the insertion port 4 (refer to FIG. 1). However, the central flat face 18 of the central top face region 15 forms a circular shape as the side wall section 19 of the central top face region 15 is pushed by an inner wall 42 (refer to FIG. 1) of the top face cap 7 on the major axis side of the ellipse when the elastic valve body 3 is housed in the insertion port 4, and accordingly, the inner surfaces of the slit 9 are brought into intimate contact with each other to close the slit 9. For the purpose of facilitating understanding of the configuration, FIG. 1 and FIGS. 6 to 10B, 14A and 14B (referred to below) illustrate the slit 9 that is not in an intimate-contact and closed state, but the inner surfaces are actually in the intimate-contact and closed state.

Herein, the central top face region 15 has a curved face 20 that connects an outer edge of the central flat face 18 and the side wall section 19 in addition to the central flat face 18 and the side wall section 19 described above as illustrated in FIGS. 2 to 5B. Specifically, the curved face 20 has a circular arc shape in a sectional view of a section (for example, a section illustrated in FIG. 5A) perpendicular to the longitudinal direction of the slit 9, and the central flat face 18 and the side wall section 19 are connected to each other via the curved face 20. The inserted male connector 100 (refer to FIG. 12) is removed in a state in which the elastic valve body 3 is attached to the housing 2 by providing the curved face 20 in the above-described manner, and the top face 10 of the elastic valve body 3 is hardly caught by the inner wall 42 (refer to FIG. 1) of the housing 2 which is positioned near an inlet of the insertion port 4 when the elastic valve body 3 having been pushed into the connector 1 (refer to FIG. 1) returns to a predetermined position by a restoring force. Further, the present embodiment is configured such that a part of the curved face 20 positioned farther from the slit 9 in the major-axis direction (direction perpendicular to the longitudinal direction of the slit 9 in FIG. 3A) of the elliptical central flat face 18 has a longer length L of the curved face 20 in the same direction as illustrated in FIG. 3A. This is because an outer edge positioned farther from the slit 9 in the major-axis direction of the elliptical central flat face 18 is more likely to be caught by the inner wall 42 of the housing 2 in the outer edge of the central flat face 18 of the central top face region 15 when the elastic valve body 3 returns to the predetermined position by the restoring force.

As illustrated in FIG. 5B, the curved face 20 having the circular arc shape is not provided on both ends of the central flat face 18 including the slit 9 when the elastic valve body 3 is viewed in a cross-section parallel to the longitudinal direction of the slit 9, and the central flat face 18 and the side wall section 19 are directly connected to each other substantially at right angles in the present embodiment, but the curved face 20 may be provided along the entire outer edge of the central flat face 18, that is, provided so as to surround the central flat face 18 when the elastic valve body 3 is viewed from the top face 10 side.

As illustrated in FIGS. 2, 5A and 5B, the peripheral section top face region 17 of the peripheral section 14 is provided with a peripheral edge flat part 21, which extends in the radial direction A and has a planar shape, and an annular side wall section 22 which is continuous to an inner edge of the peripheral edge flat part 21 and has an inner diameter in the radial direction A gradually decreasing as approaching the bottom face 11 side in the thickness direction B perpendicular to the peripheral edge flat part 21. The side wall section 22 of the present embodiment extends in a curved shape in the sectional views of FIGS. 5A and 5B, but may be configured to extend linearly in the same sectional views. In addition, the side wall section 22 of the present embodiment is configured such that the inner diameter gradually decreases in the radial direction A as approaching the bottom face 11 side in the thickness direction B, but may have a cylindrical shape which is parallel to the thickness direction B. However, when the side wall section 22 has a tapered shaped whose inner diameter gradually decreases in the radial direction A as approaching the bottom face 11 side in the thickness direction B perpendicular to the peripheral edge flat part 21 as in the present embodiment, the engaging projection 41 (refer to FIG. 6) of the top face cap 7 is guided so as to be in contact with the side wall section 19 of the central top face region 15 by the side wall section 22 of the peripheral section top face region 17, and further, to press the side wall section 19 to the insertion port 4 (refer to FIG. 6) side at the time of assembling the elastic valve body 3, and thus, variation of a position of the elastic valve body 3 in the radial direction A being held by the holding section 48 (refer to FIG. 6) is suppressed. Further, the engaging projection 41 of the top face cap 7 is guided so as to be in contact with the side wall section 19 by the side wall section 22, and further, to press the side wall section 19 inward in the radial direction, and thus, it is possible to suppress the generation of slack on the bottom face side of the central section 13 of the elastic valve body 3 as the part of the elastic valve body 3 being compressed by the holding section 48 is pushed to the insertion port 4 side at the time of holding the elastic valve body 3 using the holding section 48. The details thereof will be described below (refer to FIG. 11).

The constricted section top face region 16 of the constricted section 12 is an annular groove bottom 24 of the top face annular groove 23 which has the annular side wall section 19 of the central top face region 15 and the annular side wall section 22 of the peripheral section top face region 17, described above, as groove walls opposing each other. The engaging projection 41 (refer to FIG. 6) of the top face cap 7 (described below) enters the top face annular groove 23, is in contact with the annular groove bottom 24, and compresses the elastic valve body 3 to form the holding section 48.

The bottom face 11, which is a face on the opposite side of the top face 10 of the elastic valve body 3 and forms a part of the outer wall of the elastic valve body similarly to the top face 10, is configured of a central section bottom face region 25 of the central section 13, a constricted section bottom face region 26 of the constricted section 12, which is positioned on the outer side of the central section bottom face region 25 in the radial direction A, and a peripheral section bottom face region 27 of the peripheral section 14 which is positioned on the further outer side of the constricted section bottom face region 26 in the radial direction A.

The central section bottom face region 25 is provided with a central flat face 28 on the bottom face 11 side, which is a face parallel to the central flat face 18 on the top face 10 side, and a central projection 29 which is positioned on the outer side of the central flat face 28 in the radial direction A and projects outward than the central flat face 28 (downward in FIGS. 4A to 5B).

Although the slit 9 is not formed in the central flat face 28 on the bottom face 11 side, as described above, when the male connector 100 (refer to FIG. 12) is first inserted, for example, a part between the tip of the slit 9 formed in the central flat face 18 on the top face 10 side of the elastic valve body 3 and the central flat face 28 on the bottom face 11 side is split, which allows the slit 9 to communicate with the central flat face 18 on the top face 10 side through the central flat face 28 on the bottom face 11 side. FIG. 3B illustrates the position of the slit 9 on the top face 10 side using a broken line for the purpose of facilitating the description.

The central projection 29 projects outward than the central flat face 28, and thus, a thickness between the central flat face 18 on the top face 10 side and the central projection 29 in the thickness direction B is thicker than a thickness between the central flat face 18 on the top face 10 side and the central flat face 28 on the bottom face 11 side in the thickness direction B. When an excessive load is applied to the elastic valve body 3 during the insertion or removal of the male connector 100 or when the male connector 100 is repeatedly inserted and removed, there is a problem that a longitudinal end of the communicating slit 9 on the bottom face 11 side in a configuration that is not provided with the central projection 29, but it is possible to suppress the generation of such a problem by providing the central projection 29 and reinforcing the longitudinal end of the slit 9. In the present embodiment, the annular central projection 29 is formed so as to surround the central flat face 28 when the elastic valve body 3 is viewed from the bottom face 11 side, and each thickness of parts corresponding to both sides of the slit 9 in the longitudinal direction, formed on the top face 10, is the thickest. When such a configuration is provided, it is possible to prevent the end of the penetrating slit 9 from being split in the longitudinal direction and to ensure both an excellent insertability of the male connector into the elastic valve body 3 and maintenance of the elastic restoring force of the elastic valve body 3.

In addition, an annular side wall section 30, which has a face substantially parallel to the thickness direction B and a face inclined with respect to the thickness direction B being continuous in a circumferential direction E, is continuous to an outer edge of the central projection 29. Specifically, as illustrated in FIGS. 3B, 5A, and 5B, a part of the side wall section 30, which is positioned in a direction (minor-axis direction in FIG. 3B) perpendicular to the longitudinal direction of the slit 9 with respect to the slit 9, is configured of the surface substantially parallel to the thickness direction B, and a part of the side wall section 30 which is positioned in the longitudinal direction of the slit 9 (the major-axis direction in FIG. 3B) with respect to the slit 9 is configured of a surface whose outer diameter gradually increases in the radial direction A as approaching the top face 10 side in the thickness direction B.

As illustrated in FIGS. 5A and 5B, the peripheral section bottom face region 27 is provided with a planar peripheral edge flat part 31 extending in the radial direction A, and an annular side wall section 32 which is continuous to an inner edge of a peripheral edge flat part 31 and extends in the thickness direction B substantially perpendicular to the peripheral edge flat part 31. The side wall section 32 of the present embodiment is configured to extend in the thickness direction B in the sectional views of FIGS. 5A and 5B, but may be configured such that an inner diameter thereof gradually decreases in the radial direction A as approaching the top face 10 side in the thickness direction B. When such a configuration is provided, the engaging projection 45 (refer to FIG. 6) of the bottom face cap 8 is guided so as to be in contact with the side wall section 30 of the central section bottom face region 25 by the side wall section 32 of the peripheral section bottom face region 27, and further, to press the side wall section 30 at the time of assembling the elastic valve body 3 as will be described below, and the variation of the position of the elastic valve body 3 in the radial direction A being held by the holding section 48 (refer to FIG. 6) is suppressed. Further, the engaging projection 45 of the bottom face cap 8 is guided so as to be in contact with the side wall section 30 of the central section 13 by the side wall section 32 of the peripheral section bottom face region 27, and further, to press the side wall section 30 inward in the radial direction, and thus, it is possible to further suppress the generation of slack of the central section 13 on the bottom face 11 side of the elastic valve body 3 as the part of the elastic valve body 3 being compressed by the holding section 48 moves to the insertion port 4 side at the time of holding the elastic valve body 3 using the holding section 48 (refer to FIG. 6). Details thereof will be described below (refer to FIG. 11).

The constricted section bottom face region 26 of the constricted section 12 is an annular groove bottom 34 of a bottom face annular groove 33 which has the annular side wall section 30 of the central section bottom face region 25 and the annular side wall section 32 of the peripheral section bottom face region 27, described above, as groove walls. The engaging projection 45 of the bottom face cap 8 (described below) enters the bottom face annular groove 33, is in contact with the annular groove bottom 34, and compresses and holds the elastic valve body 3 together with the engaging projection 41 of the top face cap 7, thereby forming the holding section 48 (refer to FIG. 6).

As illustrated in FIGS. 2 to 5B, an outer edge of the peripheral section top face region 17 of the top face 10 of the elastic valve body 3 in the radial direction A and an outer edge of the peripheral section bottom face region 27 of the bottom face 11 in the radial direction A are connected to each other via an annular side wall section 35 forming the outer wall of the elastic valve body 3 together with the top face 10 and the bottom face 11. The side wall section 35 of the present embodiment is an outer peripheral face which is parallel to the thickness direction B as illustrated in FIGS. 4A to 5B.

[Top Face Cap 7]

Figure 6:
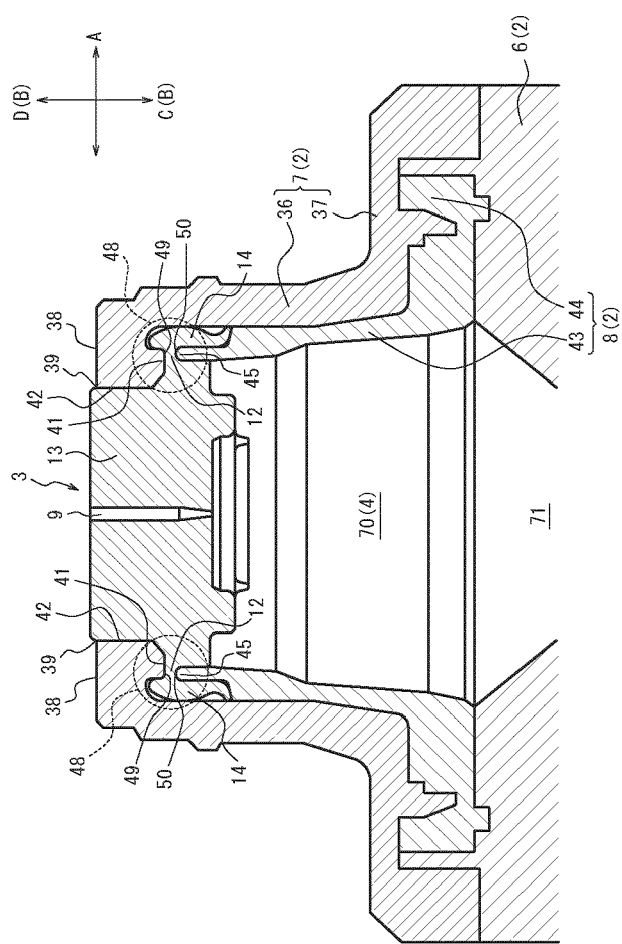
FIG. 6 is an enlarged sectional view obtained by enlarging a part of a section of FIG. 1.

FIG. 6 is an enlarged sectional view illustrating a state in which the above-described elastic valve body 3 is held by the top face cap 7 and the bottom face cap 8. Each configuration of the top face cap 7, the bottom face cap 8, and the holder 6 will be described as follows with reference to FIGS. 1 and 6.

As illustrated in FIG. 1, the top face cap 7 is configured of a, substantially cylindrical hollow barrel 36 and a flange 37 which is provided on an end of the hollow barrel 36. As illustrated in FIG. 6, an upper face (upper face in FIG. 6) on the other end of the hollow barrel 36 is formed as a planar extending section 38 which extends in the radial direction A (the same direction as a direction perpendicular to an insertion direction C of the male connector 100 in FIGS. 1 and 6) of the elastic valve body 3. The extending section 38 includes a substantially circular edge 39 which defines an end of the insertion port 4 into which the male connector 100 is inserted from the outside. A screw thread 40 is formed on an outer peripheral face of the hollow barrel 36 so as to be screwed with a lock connector which is defined by ISO 594. The flange 37 is a part which is formed to be integrated with the hollow barrel 36, and is configured such that the top face cap 7 is held by the holder 6 as the flange 37 is engaged with the holder 6 (described below).

As illustrated in FIG. 6, the engaging projection 41, which projects toward the insertion direction C of the male connector 100, enters the top face annular groove 23 (refer to FIGS. 2 to 3B, 5A and 5B) of the elastic valve body 3 described above, and compresses the elastic valve body 3 together with the engaging projection 45 of the bottom face cap 8, is provided near the edge 39 of an inner wall of the hollow barrel 36. The annular inner wall 42 of the top face cap 7, formed between the edge 39 and the engaging projection 41, is configured so as to be in contact with the side wall section 19 (refer to FIGS. 2 to 5B) of the central top face region 15 of the elastic valve body 3, described above, in a state in which the male connector 100 is not inserted, and to be in contact with the male connector 100 in a state in which the male connector 100 is inserted (refer to FIG. 12). That is, the central top face region 15 (refer to FIGS. 2 to 5B) of the elastic valve body 3 is fit into a substantially columnar space surrounded by the inner wall 42 in the state in which the male connector 100 is not inserted, and the male connector 100 is fit with the top face cap 7 by the cylindrical inner wall 42 in the state in which the male connector 100 is inserted. The inner wall 42 according to the present embodiment has a cylindrical shape which is parallel to the insertion direction C, but may have a tapered shape whose inner diameter is gradually slimmer in the insertion direction C in accordance with the outer shape of the male connector 100.

In addition, the central flat face 18 of the central top face region 15 of the elastic valve body 3, which extends in the radial direction A of the elastic valve body 3, is positioned on a reverse direction D side of the insertion direction C of the male connector than the edge 39 in the state in which the male connector 100 is not inserted as illustrated in FIG. 6. That is, a part of the central top face region 15 projects toward the reverse direction D than the edge 39.

Even if the elastic valve body 3 is somewhat pushed into the connector 1 (in the insertion direction C of the male connector 100) when a user such as a health care professional wipes off a liquid medicine or the like adhering near on the top face 10, which is the outer wall of the elastic valve body 3, a step (step that causes the inner wall 42 to expose to the outside) is hardly formed between the central top face region 15 of the elastic valve body 3 and the edge 39 of the top face cap 7 due to such push by providing the above-described configuration, and thus, it is easy to wipe off the liquid medicine or the like.

[Bottom Face Cap 8]

As illustrated in FIG. 1, the bottom face cap 8 is configured to include a substantially cylindrical hollow barrel 43 and a flange 44 which is provided on an end of the hollow barrel 43 similarly to the top face cap 7. The engaging projection 45, which projects toward the reverse direction D, which is reverse to the insertion direction C of the male connector 100, enters the bottom face annular groove 33 (refer to FIGS. 3B, 5A and 5B) of the elastic valve body 3, described above, and compresses and holds the elastic valve body 3 together with the engaging projection 41 of the top face cap 7, is provided on the other end of the hollow barrel 43 (refer to FIG. 6).

The bottom face cap 8 is held by the top face cap 7 by being ultrasonic-bonded to an inner face of the hollow barrel 36 and/or a lower face (lower face in FIG. 1) of the flange 37 of the top face cap 7, and further, is fixedly positioned by supporting the flange 44 of the bottom face cap 8 by the holder 6 (described below).

[Holder 6]

As illustrated in FIG. 1, the holder 6 supports the top face cap 7 and the bottom face cap 8, and defines a hollow section 71 inside thereof. Although the holder 6 of the present embodiment supports both the top face cap 7 and the bottom face cap 8 through direct contact, it may be configured such that, for example, the holder 6 is not in contact with the top face cap 7 but in direct-contact only with the bottom face cap 8, and the top face cap 7 is in contact with and supported by the bottom face cap 8. That is, it may be configured such that the holder 6 is in direct contact with and supports anyone between the top face cap 7 and the bottom face cap 8, and is not in direct-contact with the other. The members being in direct-contact with each other are preferably bonded to each other by, for example, ultrasonic-bonding or the like.

In addition, the insertion port 4 (hollow section 70), which is defined by the inner wall of the top face cap 7 and the inner wall of the bottom face cap 8, and the hollow section 71 communicate with each other in the state in which the male connector 100 is not inserted. Here, the "communication" between the insertion port 4 and the hollow section 71 means that both the spaces are connected, and includes not only direct connection between the spaces, but also connection between the spaces through another space. The insertion port 4 and the hollow section 71 according to the present embodiment, illustrated in FIG. 1, are configured to be directly connected.

In addition, in the state in which the male connector 100 is inserted into the connector 1, a tip 101 of the male connector 100 enters or is inserted to the vicinity of the hollow section 71 through the insertion port 4, and a liquid flow path inside the male connector 100 and the hollow section 71 of the holder 6 communicate with each other, which will be described in detail below.

As illustrated in FIG. 1, the holder 6 according to the present embodiment is provided with an outer cylindrical section 46 which has a substantially cylindrical shape and is provided with a screw thread for a lock connector on an inner peripheral face thereof, and a male luer section 47 which is provided in a hollow section that is defined by the outer cylindrical section 46, and various holders can be used without being limited to such a shape of the holder 6, and can be suitably changed according to a use application of the user or the like. For example, a connector 110 provided with a holder 60 as illustrated in FIG. 7A may be used. The holder 60 is provided with a holder main body 61, which is formed of a substantially cylindrical casing having a hollow section therein, and cylindrical upstream port 62 and downstream port 63 which project from an outer peripheral face of the holder main body 61. The hollow inside the holder main body 61 serves as a part of a liquid flow path 64 from the upstream port 62 to the downstream port 63. In addition, the top face cap 7 and the bottom face cap 8 are supported on an outer wall of the holder 60. A shape of the liquid flow path inside the holder 60 illustrated in FIG. 7A and an outer shape thereof formed along the shape of the liquid flow path are different from those of the holder 6, but the elastic valve body 3, the top face cap 7, and the bottom face cap 8, which are the same as those described above, can be used.

Figure 7B:
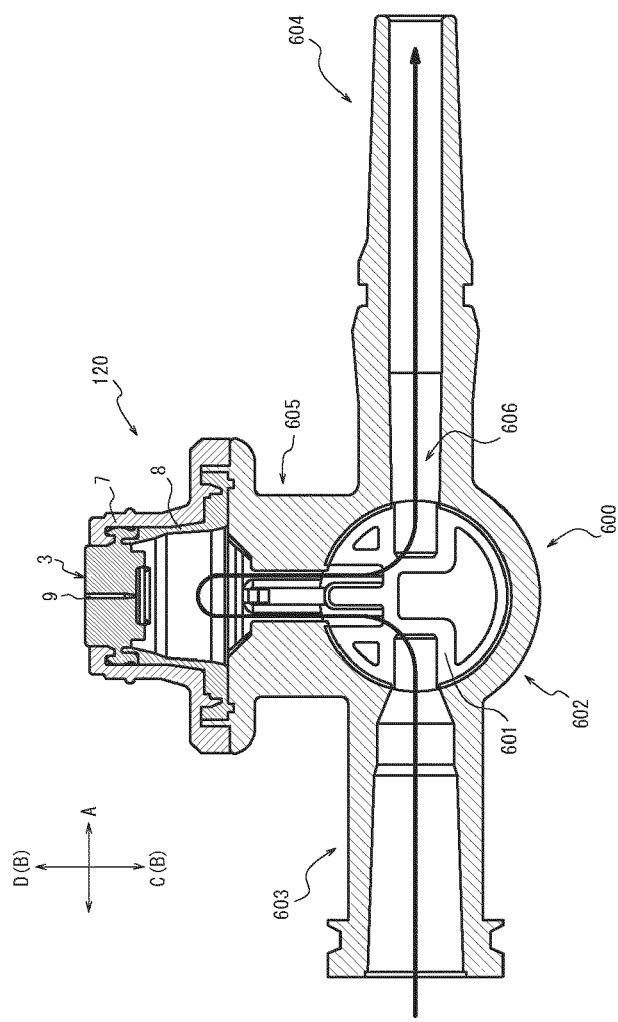
FIG. 7B is a sectional view illustrating a connector provided with a holder which has a different shape from the holder of FIG. 1 or 6 among the holders that can be applied to the present invention.

In addition, a holder 600 illustrated in FIG. 7B can be used instead of the holder 6 other than the above-described holder 60. FIG. 7B illustrates a three-way stopcock as a connector 120. The holder 600 in the three-way stopcock is provided with a substantially cylindrical holder main body 602 which houses a cock 601 therein, a substantially cylindrical upstream port 603 provided on an outer wall of the holder main body 602, a substantially cylindrical downstream port 604 provided on the outer wall of the holder main body 602 at a position on the opposite side of the upstream port 603 with the holder main body 602 sandwiched therebetween, and a branch port 605 provided on the outer wall of the holder main body 602 at a position different from the positions of the upstream port 603 and the downstream port 604. It is possible to form a liquid flow path 606 as indicated by an arrow in FIG. 7B inside the holder 600. The elastic valve body 3, the top face cap 7, and the bottom face cap 8 are provided on an end of the branch port 605 of the holder 600 illustrated in FIG. 7B, and are supported by the holder 600.

Herein, the present embodiment has the configuration in which the elastic valve body 3 is held by the top face cap 7 and the bottom face cap 8 forming the cap 5, but is not limited to such a configuration. For example, the bottom face cap 8 and the holder 6 may be configured using a single member to cause the holder 6 to serve the function of the bottom face cap 8 and the elastic valve body 3 may be held using the top face cap 7 forming the cap 5 and the holder 6. In addition, the bottom face cap 8 and the holder 60 may be configured using a single member by employing the shape of the holder 60 instead of the shape of the holder 6, or the bottom face cap 8 and the holder 600 may be configured using a single member by employing the shape of the holder 600 instead of the shape of the holder 6.

[Holding Section 48 to Hold Elastic Valve Body 3]

Next, a description will be given regarding the configuration of compressing and holding the elastic valve body 3 using the top face cap 7 and the bottom face cap 8.

As illustrated in FIG. 6, the elastic valve body 3 is attached to close the hollow section 70 (insertion port 4) which is defined by the hollow barrel 36 of the top face cap 7 and the hollow barrel 43 of the bottom face cap 8. Specifically, the holding section 48 is fixedly positioned inside the hollow section 70 of the elastic valve body 3 by being in contact with the top face 10 in which the slit 9 of the elastic valve body 3 is formed and the bottom face 11 on the opposite side of the top face 10 and holding the elastic valve body 3. More specifically, the engaging projection 41 of the top face cap 7 enters the top face annular groove 23 (refer to FIGS. 5A and 5B and the like) of the elastic valve body 3, then, the engaging projection 45 of the bottom face cap 8 enters the bottom face annular groove 33 of the elastic valve body 3, and the holding section 48 is formed by compressing the elastic valve body 3 using the groove bottom 24 (refer to FIGS. 5A and 5B and the like) of the top face 10 and the groove bottom 34 of the bottom face 11 and is fixedly positioned in the hollow section 70 of the elastic valve body 3. The constricted section 12 of the elastic valve body 3 according to the present embodiment has a thickness of about 1.0 mm in the thickness direction B in the state before being held by the holding section 48, and is compressed to a thickness (for example, 0.2 to 0.3 mm) that makes it difficult to be elastically deformed in the thickness direction B by the compression of the holding section 48, but such an amount of compression is illustrative, and can be suitably changed according to a shape, a size or the like of the elastic valve body.

Herein, the holding section 48 is configured of a top-face-side holding section 49, which is in contact with the top face 10 of the elastic valve body 3, and a bottom-face-side holding section 50 which is in contact with the bottom face 11 of the elastic valve body 3 and holds the elastic valve body 3 together with the top-face-side holding section 49, and the holding section 48 is provided in a substantially circular shape to surround the slit 9 when the elastic valve body 3 is viewed from the top face 10 side. The top-face-side holding section 49 according to the present embodiment is a tip of the engaging projection 41 of the top face cap 7, and the bottom-face-side holding section 50 is a tip of the engaging projection 45 of the bottom face cap 8. In addition, the "case of being viewed from the top face 10 side" of the elastic valve body 3 means a case in which the top-face-side holding section 49 and the bottom-face-side holding section 50 are projected on a virtual plane obtained when the elastic valve body 3 is viewed from the top face 10, and does not mean whether or not it is actually viewable.

The elastic valve body 3 in the state of being held by the holding section 48 is provided with the constricted section 12 which is held by the holding section 48, the central section 13 which is positioned on the inner side in the radial direction A than the constricted section 12, and the peripheral section 14 which is positioned on the outer side, in the radial direction A, of the constricted section 12 in the case of being viewed from the top face 10 side.

In the same state, the peripheral section 14 of the elastic valve body 3 is surrounded by a partial inner wall of the top face cap 7 and a partial outer wall of the bottom face cap 8. Details thereof will be described below (refer to FIGS. 8A and 8B and the like).

In addition, the holding section 48 according to the present embodiment is provided over the entire region of the elastic valve body 3 in a circumferential direction E (refer to FIGS. 3A and 3B) when the elastic valve body 3 is viewed from the top face 10 side, but can be configured to be provided only in a part in circumferential direction E, for example, arranged to be spaced at predetermined intervals in the circumferential direction E with pectinate projections. However, when the holding section 48 is provided in the entire region in the circumferential direction E to be in contact with the top face 10 and the bottom face 11 of the elastic valve body 3 in the entire region in the circumferential direction E as in the present embodiment, it is possible to further prevent the constricted section 12 and the peripheral section 14 of the elastic valve body 3 from moving to the insertion port 4 side against the repeated insertion and removal of the male connector.

Further, the holding section 48 of the present embodiment is configured of the housing 2. Specifically, the holding section 48 of the present embodiment is configured of a tip of the engaging projection 41 of the top face cap 7 and a tip of the engaging projection 45 of the bottom face cap 8, but the shape of the holding section 48 is not limited thereto. For example, a holding section may be configured using members other than the members forming a housing. In addition, the holding section is not limited to the mode of the holding section 48 according to the present embodiment even when being configured of the housing, and for example, the housing is provided with a top-face-side member positioned on a top face side of an elastic valve body, a bottom-face-side member positioned on a bottom face side of the elastic valve body, and a contact member, which is positioned between the top-face-side member and the bottom-face-side member and is held therebetween to be in direct-contact with the top face and the bottom face of the elastic valve body to hold the elastic valve body, and this contact member may form a holding section. In such a case, the holding section is formed by providing the contact member to be sandwiched between the top-face-side member and the bottom-face-side member, and thus, the configuration is provided in which the top-face-side member and the bottom-face-side member are not in direct-contact with the top face and the bottom face of the elastic valve body.

[Regarding Volume of Peripheral Section 14 of Elastic Valve Body 3]

Next, a description will be given regarding a relationship between a volume of the peripheral section 14 in the state in which the elastic valve body 3 is held by the holding section 48 of the housing 2, in other words, the top-face-side holding section 49 and the bottom-face-side holding section 50 which are configured using the engaging projections 41 and 45 of the top face cap 7 and the bottom face cap 8, and a volume of the peripheral section 14 in the state in which the elastic valve body 3 is not held by the holding section 48.

The "state in which the elastic valve body is held by the holding section" means a state in which the elastic valve body is assembled inside the connector so as to be used as the connector by a user such as a health care professional as illustrated in FIG. 1 or the like. In addition, the "state in which the elastic valve body is not held by the holding section" means a state in which the elastic valve body is not assembled inside the connector, that is, the state of the elastic valve body alone as illustrated in FIGS. 2 to 5B, for example.

A volume V1 of the peripheral section 14 in the state in which the elastic valve body 3 is held by the holding section 48 is larger than a volume V2 of the peripheral section 14 in the state in which the elastic valve body 3 is not held by the holding section 48 in the present embodiment.

Figure 14A:
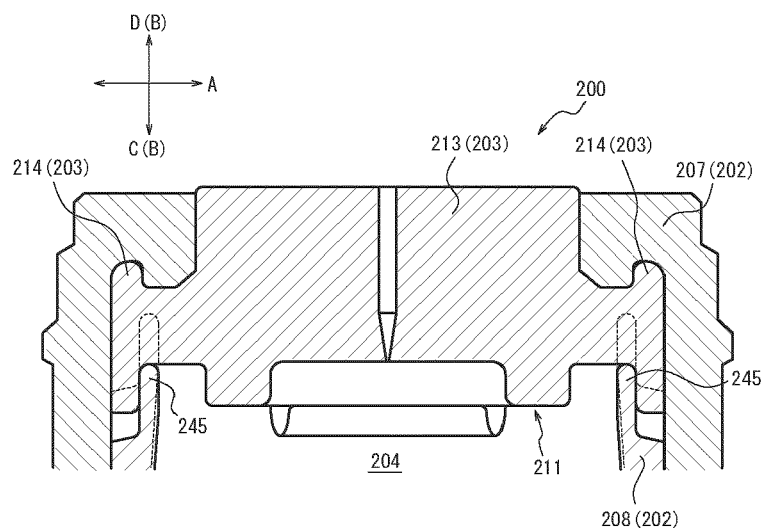
FIGS. 14A and 14B are sectional views of a connector as a comparative example.
Figure 14B:
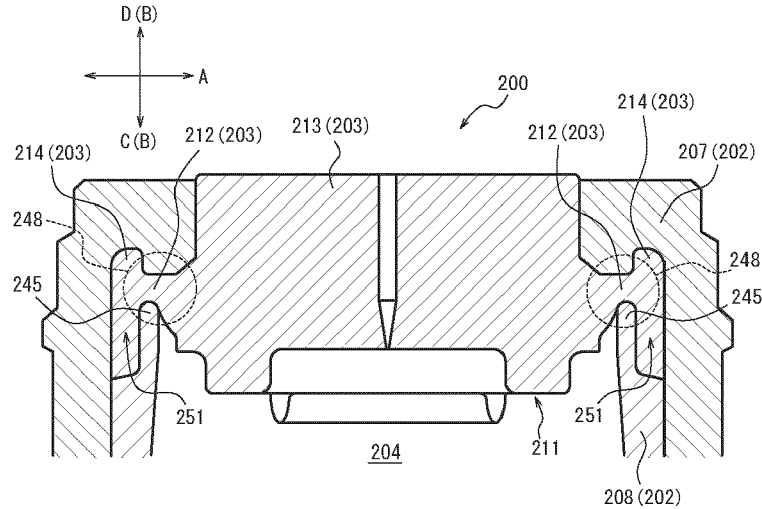

First, a description will be given regarding a connector 200 as a comparative example of the connector 1 according to the present embodiment. FIGS. 14A and 14B illustrate the connector 200 as the comparative example. The connector 200 is different from the connector 1 as the present embodiment in terms that a volume of a peripheral section is not changed before and after an elastic valve body is held by a holding section. FIG. 14A illustrates a state in which an elastic valve body 203 of the connector 200 is not held by a holding section 248, and FIG. 14B illustrates a state in which the elastic valve body 203 is held by the holding section 248. A broken line of FIG. 14A illustrates a position of a bottom face cap 208 in a state in which the elastic valve body 203 is held by the holding section 248.

As illustrated in FIGS. 14A and 14B, a peripheral section 214 of the elastic valve body 203 in the state in which the elastic valve body 203 is not held by the holding section 248, is larger than a housing space 251 (a space which is defined by a top face cap 207 of a solid line and the bottom face cap 208 of the broken line in FIG. 14A, and a space which is defined by the top face cap 207 of the solid line and the bottom face cap 208 of the broken line in FIG. 14B) in the state in which the elastic valve body 203 is held by the holding section 248. That is, the peripheral section 214 of the elastic valve body 203 is compressed by a wall face that defines the housing space 251, and the volume thereof decreases when the state illustrated in FIG. 14A in which the elastic valve body 203 is not held by the holding section 248 is changed to the state illustrated in FIG. 14B in which the elastic valve body 203 is held by the holding section 248.

Thus, a part of the elastic valve body 203, which is pushed in the radial direction A from a position of a constricted section 212 by compression of the holding section 248, is likely to be pushed toward a central section 213 side instead of the peripheral section 214 side, and there is a risk that slack on a bottom face 211 side of the central section 213 occurs as illustrated in FIG. 14B. When there is the slack as illustrated in FIG. 14B, a force to pull the central section 213 of the elastic valve body 203 to the peripheral section 214 side in the radial direction A becomes weak as compared to a configuration in which there is no slack, and there is a possibility that the central section 213 of the elastic valve body 203 is stretched at the time of repeatedly performing insertion and removal of a male connector. When the central section 213 of the elastic valve body 203 is stretched, there is a risk that the central section 213 is hardly restored to its original position even after removing the male connector.

Figure 12:
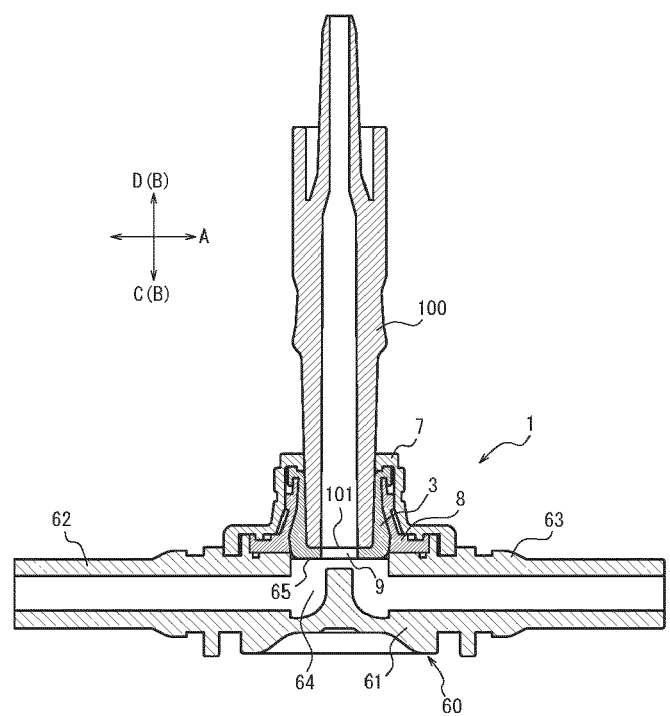
FIG. 12 is a sectional view illustrating a state in which a male connector is inserted into a connector according to the present invention.

In addition, if there is the slack as illustrated in FIG. 14B, a volume of the elastic valve body 203 that is sandwiched by the male connector 100 and the inner walls of the top face cap 207 and the bottom face cap 208 increases when the male connector 100 as illustrated in FIG. 12 is inserted into the connector 200. As a result, the insertion resistance of the male connector 100 increases, and there is a risk that the insertability of the male connector 100 deteriorates. Further, there is also a possibility that an abrasion is formed in the elastic valve body 203, and there is a risk that s worn valve body piece becomes a foreign substance or a risk that the restoring force of the elastic valve body 203 deteriorates when the abrasion is formed in the elastic valve body 203.

On the contrary, the connector 1 as the present embodiment is configured to increase the volume of the peripheral section 14 of the elastic valve body 3, as described above, when the elastic valve body 3 is changed from the state of not being held to the state of being held by the holding section 48, and thus, the slack of the central section 13 on the bottom face 11 side hardly occurs, which is different form the connector 200 as the comparative example described above. Hereinbelow, a description will be given in details regarding a change in volume of the peripheral section 14 of the elastic valve body 3 in the connector 1 as the present embodiment.

Figure 8A:
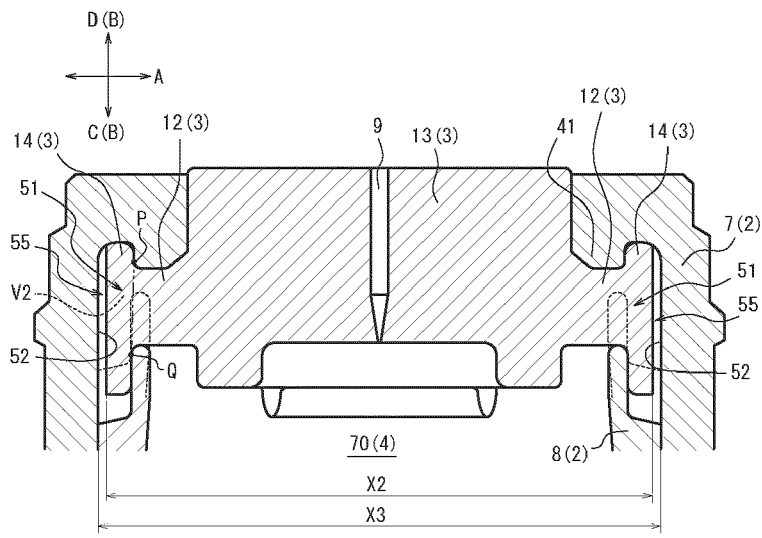
FIG. 8A is a sectional view illustrating a state before the elastic valve body is held by a holding section.
Figure 8B:
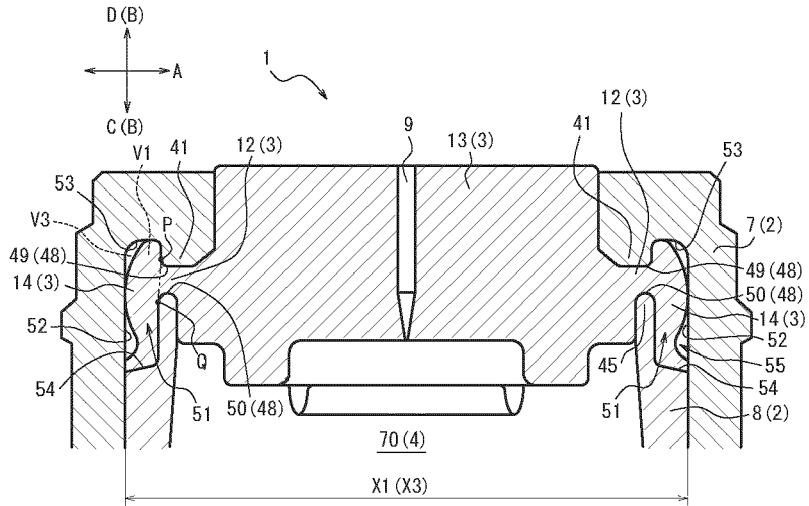
FIG. 8B is a sectional view illustrating a state in which the elastic valve body is held by the holding section.

FIGS. 8A and 8B are diagrams illustrating the change in volume of the peripheral section 14 of the elastic valve body 3 between the states of the elastic valve body 3 being held and not being held by the holding section 48 in the connector 1 as the present embodiment. Specifically, FIG. 8A illustrates a state immediately before the elastic valve body 3, the top face cap 7, and the bottom face cap 8 are assembled, that is, the state in which the elastic valve body 3 is not held by the holding section 48, and FIG. 8B illustrates a state in which the elastic valve body 3 is assembled inside the connector 1, that is, the state in which the elastic valve body 3 is held by the holding section 48.

As illustrated in FIGS. 8A and 8B, a partial volume of the elastic valve body 3 is moved outward in the radial direction A when the constricted section 12 of the elastic valve body 3 is compressed by the holding section 48, and thus, the volume of the peripheral section 14 of the elastic valve body 3 increases as compared to that of the state before the constricted section 12 is compressed by the holding section 48.

Specifically, the housing 2 defines an annular housing space 51 in which the peripheral section 14 of the elastic valve body 3 can be housed as illustrated in FIGS. 8A and 8B. More specifically, the housing 2 is provided with an inner wall section 52, which surrounds the perimeter of the elastic valve body 3 in the radial direction A on the outer side of the peripheral section 14 in the radial direction A in the state in which the elastic valve body 3 is held by the holding section 48, and the housing space 51 is defined by the inner wall section 52, the top-face-side holding section 49, the bottom-face-side holding section 50, a top-face-side coupling section 53, which connects an end (an end on a side of the reverse direction D of the insertion direction C of the mail connector in FIGS. 8A and 8B) of the inner wall section 52 and the top-face-side holding section 49, and a bottom-face-side coupling section 54, which connects the other end (an end on a side of the insertion direction C in FIGS. 8A and 8B) of the inner wall section 52 and the bottom-face-side holding section 50, in a section perpendicular to the radial direction A (section not only parallel to the thickness direction B but also parallel to the insertion direction C of the male connector).

FIG. 8A is a diagram illustrating the state in which the elastic valve body 3 is not held by the holding section 48, and illustrates a position of the engaging projection 45 of the bottom face cap 8 in the state in which the elastic valve body 3 is held by the holding section 48 using a broken line. As illustrated in FIG. 8A, when an outer wall of the peripheral section 14 of the elastic valve body 3 in the state of not being held by the holding section 48 and a wall face (a partial inner wall of the top face cap 7 indicated by the solid line and a partial outer wall of the bottom face cap 8 indicated by the broken line in FIG. 8A) that defines the housing space 51 in the state in which the elastic valve body 3 is held by the holding section 48 are viewed, a gap 55 is provided therebetween in the present embodiment. In other words, the volume V2 of the peripheral section 14 in the state in which the elastic valve body 3 is not held by the holding section 48 (refer to FIG. 8A) is smaller than a volume V3 of the housing space 51 in the state in which the elastic valve body 3 is held by the holding section 48 (refer to FIG. 8B).

Accordingly, when the elastic valve body 3 is changed from the state of FIG. 8A to the state of being held by the holding section 48 illustrated in FIG. 8B, the constricted section 12 is compressed and deformed by compression of the engaging projection 41 of the top face cap 7 and the engaging projection 45 of the bottom face cap 8, and further, a part of the elastic valve body 3 is moved from the position of the constricted section 12 to be pushed to the peripheral section 14 side in the radial direction A. That is, the volume relationship of V2<V3 is provided as in the present embodiment, it is possible to cause a part of the elastic valve body 3 moving from the constricted section 12 to be easily moved to the peripheral section 14 side as compared to a configuration having a volume relationship of V2≥V3. Thus, a part of the elastic valve body 3 is moved from the position of the constricted section 12 to the central section 13 side when the elastic valve body 3 is changed from the state illustrated in FIG. 8A to the state illustrated in FIG. 8B, that is, when being assembled to the connector 1, and accordingly, the central section 13 on the rear face 11 side is prevented from being slack.

In other words, the peripheral section 14 in the state in which the elastic valve body 3 is held by the holding section 48 is in a state in which a part of the elastic valve body 3 is pushed and moved from the position of the constricted section 12 by compression of the holding section 48, and thus, the volume V1 of the peripheral section 14 in the state in which the elastic valve body 3 is held by the holding section 48 is larger than the volume V2 of the peripheral section 14 in the state in which the elastic valve body 3 is not held by the holding section 48.

The peripheral section 14 of the elastic valve body 3 is a part which is positioned on the outer side of a position of the elastic valve body 3 that is held by the holding section 48 when the elastic valve body 3 is viewed from the top face 10 side. Herein, the "position of being held by the holding section" of the elastic valve body 3 means a position of the elastic valve body 3 which is held by the top-face-side holding section 49 and the bottom-face-side holding section 50. Accordingly, the "peripheral section of the elastic valve body" means a part which is positioned on the outer side, in the radial direction, of a line segment obtained by connecting an outermost position of the top-face-side holding section in the radial direction and an outermost position of the bottom-face-side holding section in the radial direction.

Specifically, the peripheral section 14 of the elastic valve body 3 according to the present embodiment is a part on the outer side in the radial direction A with respect to a virtual line (refer to a two-dot chain line in FIG. 8B) obtained by connecting a point P of the top-face-side holding section 49 positioned on the outermost side in the radial direction A and a point Q of the bottom-face-side holding section 50 positioned on the outermost side in the radial direction A in the state in which the elastic valve body 3 is held by the holding section 48 in sectional views illustrated in FIGS. 1 and 6 (a section which passes through a midpoint of the slit 9 in the longitudinal direction and is parallel to the thickness direction B of the elastic valve body 3 when the elastic valve body 3 is viewed from the top face 10 side).

It is possible to specify the position of the elastic valve body 3 being held by the holding section 48 according to the above-described method, and accordingly, it is also possible to specify the peripheral section 14 of the elastic valve body 3. The peripheral section 14 in the state in which the elastic valve body 3 is not assembled inside the connector 1 is specified by specifying a position of the elastic valve body 3 being held by the holding section 48 at the time of being assembled inside the connector 1 (refer to a two-dot chain line in FIG. 8A).

In this manner, it is possible to compare the volume of the peripheral section 14 of the elastic valve body 3 between the states of the elastic valve body 3 being held and not being held by the holding section 48.

Next, a description will be given in more details regarding the peripheral section 14 and the housing space 51 of the elastic valve body 3 according to the present embodiment illustrated in FIGS. 8A and 8B. As illustrated in FIG. 8B, the gap 55 is maintained between the outer wall of the peripheral section 14 of the elastic valve body 3 and the wall face that defines the housing space 51 even in the state in which the elastic valve body 3 is held by the holding section 48 in the present embodiment. In other words, the gap 55 is defined by the inner wall of the housing 2 that defines the housing space 51 and the outer wall of the peripheral section 14 even in the state in which the elastic valve body 3 is held by the holding section 48.

When the configuration is provided such that the volume of the peripheral section 14 of the elastic valve body 3 increases by compressing and holding the constricted section 12 of the elastic valve body 3 using the holding section 48, it may be configured such that the entire outer wall of the peripheral section 14 of the elastic valve body 3 is in contact with the entire wall face that defines the housing space 51 and the gap 55 is not provided therebetween in the state in which the elastic valve body 3 is held by the holding section 48. However, it is preferable to provide the configuration as in the present embodiment such that the gap 55 is maintained between the outer wall of the peripheral section 14 of the elastic valve body 3 and the wall face that defines the housing space 51 even in the state in which the elastic valve body 3 is held by the holding section 48.

When it is configured such that the entire outer wall of the peripheral section 14 of the elastic valve body 3 is in contact with the entire wall face that defines the housing space 51, and the peripheral section 14 presses the wall face that defines the housing space 51 in the state in which the elastic valve body 3 is held by the holding section 48, the housing space 51 is filled with the peripheral section 14 due to an increase of the volume of the peripheral section 14 of the elastic valve body 3 during the process of holding and compressing the elastic valve body 3 using the holding section 48. That is, the peripheral section 14 of the elastic valve body 3 is compressed deformed by the entire wall face that defines the housing space 51 before the holding (compression of the constricted section 12) of the elastic valve body 3 using the holding section 48 is completed (before the assembly of the elastic valve body 3 inside the connector 1 is completed), and a reaction force is loaded from the wall face. When the holding of the elastic valve body 3 using the holding section 48 is continued in such a state, a part of the elastic valve body 3 is likely to be pushed to the central section 13 side in the radial direction A due to the reaction force from the wall face that defines the housing space 51. That is, when the configuration illustrated in the present embodiment is provided such that the gap 55 is maintained between the outer wall of the peripheral section 14 and the wall face that defines the housing space 51 in the state in which the elastic valve body 3 is held by the holding section 48, it is possible to further suppress the slack of the central section 13 on the bottom face 11 side as compared to a configuration in which the gap 55 is not provided in the same state.

Next, a description will be given in detail regarding a position of the gap 55 with respect to the peripheral section 14 of the elastic valve body 3 in the state in which the elastic valve body 3 is not held by the holding section 48. As illustrated in FIG. 8A, the gap 55 is provided between the inner wall section 52, which surrounds the perimeter of the elastic valve body 3 in the radial direction A on the outer side of the peripheral section 14 in the radial direction A, and the outer wall of the peripheral section 14 of the elastic valve body 3 in the present embodiment. This is because a part of the elastic valve body 3 is pushed outward in the radial direction A from the position of the constricted section 12, and the side wall section 35 of the peripheral section 14 easily bulges outward in the radial direction A when the constricted section 12 of the elastic valve body 3 is compressed by the holding section 48. In particular, the side wall section 35 of the peripheral section 14 is more likely to bulge outward in the radial direction A when the elastic valve body 3 is compressed and held by the holding section 48 in a configuration in which a width of the peripheral section 14 of the elastic valve body 3 in the radial direction A is relatively thin (for example, 1 mm or less) as in the present embodiment, and thus, it is advantageous to provide the gap between the inner wall section 52 and the side wall section 35 of the peripheral section 14 of the elastic valve body 3.

As illustrated in FIG. 8B, the present embodiment is configured such that a part of the side wall section 35 of the peripheral section 14 and a part of the inner wall section 52 are in contact with each other in the state in which the elastic valve body 3 is held by the holding section 48, and the gap 55 is still provided between the peripheral section 14 and the inner wall section 52. It may be configured such that the outer wall of the peripheral section 14 and the entire inner wall section 52 are in contact with each other and the gap 55 is not provided therebetween in the state in which the elastic valve body 3 is held by the holding section 48, but it is preferable to provide the configuration illustrated in the present embodiment such that the gap 55 is maintained in the same state as described above.

Further, the present embodiment is configured such that the width of the peripheral section 14 in the radial direction A is relatively thin, and thus, a part of the side wall section 35 of the peripheral section 14, which is positioned on the outer side in the radial direction A with respect to the constricted section 12 of the elastic valve body 3 (a part which is positioned at the position of the constricted section 12 in the thickness direction B), bulges outward the most as the elastic valve body 3 is compressed by the holding section 48. Further, the present embodiment is configured such that this part of the side wall section 35 is in contact with a part of the inner wall section 52 in the state in which the elastic valve body 3 is held by the holding section 48, but it is more preferable to configure the part of the side wall section 35 not to be in contact with the inner wall section 52. Such a configuration is easily realized by employing a top face cap 700 as illustrated in FIG. 9, for example, which has a different shape from the top face cap 7 according to the present embodiment.

Figure 9:
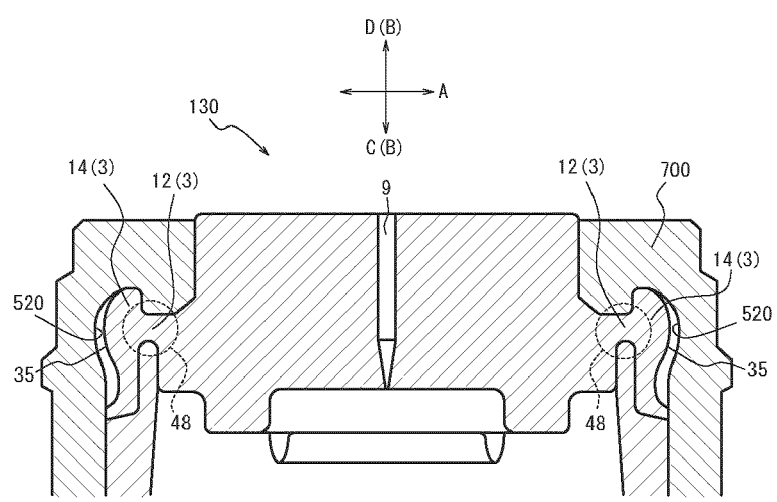
FIG. 9 is a sectional view of a connector provided with a top face cap which has a different shape from a top face cap of FIGS. 8A and 8B among top face caps that can be applied to the present invention.

The top face cap 700 of a connector 130 illustrated in FIG. 9 is provided with an inner wall section 520 in a cross-section parallel to the thickness direction B of the elastic valve body 3, which is similar to the top face cap 7. However, the inner wall section 520 of the top face cap 700 illustrated in FIG. 9 has a curved shape that projects outward in the radial direction A such that an inner diameter thereof is maximum at a position on the outer side in the radial direction A with respect to the constricted section 12 in the same sectional view, while the inner wall section 52 of the top face cap 7 is straight to be substantially parallel to the thickness direction B in the sectional views of FIGS. 1 and 6.

When such a configuration is provided, the inner diameter of the inner wall section 520 of the top face cap 700 becomes maximum at the position on the outer side in the radial direction A with respect to the constricted section 12. Thus, it is possible to prevent a part of the side wall section 35 of the peripheral section 14, which is positioned on the outer side in the radial direction A with respect to the constricted section 12 of the elastic valve body 3, from being in contact with the inner wall section 520 in the state in which the elastic valve body 3 is held by the holding section 48.

As illustrated in FIG. 9, the inner wall section 520 of the top face cap 700 has the curved shape projecting outward in the radial direction A such that the inner diameter thereof becomes maximum at the position on the outer side in the radial direction A with respect to the constricted section 12, but is not limited to the configuration of the inner wall section 520 of the top face cap 700 illustrated in FIG. 9 as long as it is configured such that a part of the side wall section 35 of the peripheral section 14, which is positioned on the outer side in the radial direction A with respect to the constricted section 12, is not in contact with the inner wall section.

In addition, the connectors 1 and 130 illustrated, respectively, in FIGS. 8A and 8B, and 9, have each configuration in which a part of the side wall section 35 of the peripheral section 14 is in contact with each part of the inner wall sections 52 and 520 in the state in which the elastic valve body 3 is held by the holding section 48, but the side wall section 35 may be configured not to be in contact with the inner wall section 52 or 520 at all.

As described above, the volume of the peripheral section 14 is changed before and after the elastic valve body 3 is held by the holding section 48 in the connector 1 as the present embodiment, but this change in volume can be described as a change in outer diameter of the elastic valve body 3 in the radial direction A. That is, a maximum outer diameter X1 of the elastic valve body 3 in the state in which the elastic valve body 3 is held by the holding section 48 is larger than a maximum outer diameter X2 of the elastic valve body 3 in the state of not being held by the holding section 48 (refer to FIGS. 8A and 8B). The "maximum outer diameter of the elastic valve body" means an outer diameter of the elastic valve body in the case of projecting the elastic valve body on a virtual plane obtained when the elastic valve body is viewed from the top face side.

In addition, a part of the side wall section 35 of the peripheral section 14, which is positioned on the outer side in the radial direction A with respect to the constricted section 12 of the elastic valve body 3 relatively easily bulges when the elastic valve body 3 is held and compressed by the holding section 48 as described above (refer to FIG. 9). Accordingly, it is also possible to describe the above-described volume change of the peripheral section 14 using the outer diameter of the elastic valve body 3 in a cross-section parallel to the radial direction A including the constricted section 12 in the state of being held by the holding section 48, and the outer diameter of the elastic valve body 3 in a cross-section parallel to the radial direction A including the constricted section 12 in the state of not being held by the holding section 48, other than the relationship between the maximum outer diameters X1 and X2 before and after the elastic valve body 3 is held by the holding section 48.

Specifically, it is configured such that the outer diameter of the elastic valve body 3 in the cross-section parallel to the radial direction A including the constricted section 12 in the state of being held by the holding section 48 is larger than the outer diameter of the elastic valve body 3 in the cross-section parallel to the radial direction A including the constricted section 12 in the state of not being held by the holding section 48 (refer to FIGS. 8A and 8B).

Further, the volume change of the peripheral section 14 before and after the elastic valve body 3 is held by the holding section 48 can be expressed as a relationship between an inner diameter of the inner wall section 52 and the outer diameter of the elastic valve body 3. That is, a maximum inner diameter X3 of the inner wall section 52 is larger than the maximum outer diameter X2 of the elastic valve body 3 in the state in which the elastic valve body 3 is not held by the holding section 48 (refer to FIG. 8A).

The inner wall section 52 of the present embodiment has a substantially cylindrical shape, and thus, the inner diameter of the inner wall section 52 is substantially equal at an arbitrary position in the insertion direction C of the male connector, and this inner diameter becomes the maximum inner diameter X3 of the inner wall section 52.

In addition, a part of the side wall section 35 of the peripheral section 14, which is positioned on the outer side in the radial direction A with respect to the constricted section 12 of the elastic valve body 3 relatively easily bulges when the elastic valve body 3 is held and compressed by the holding section 48 as described above (refer to FIG. 9). Accordingly, it is also possible to express the above-described volume change of the peripheral section 14 using the inner diameter of the inner wall section 52 in a cross-section parallel to the radial direction A including the constricted section 12 in the state of being held by the holding section 48, and the outer diameter of the elastic valve body 3 in a cross-section parallel to the radial direction A including the constricted section 12 in the state of not being held by the holding section 48, other than the relationship between the maximum inner diameter X3 of the inner wall section 52 and the maximum outer diameter X2 of the elastic valve body 3. Specifically, it is configured such that the inner diameter of the inner wall section 52 in the cross-section parallel to the radial direction A including the constricted section 12 in the state of being held by the holding section 48 is larger than the outer diameter of the elastic valve body in the cross-section parallel to the radial direction A including the constricted section 12 in the state of not being held by the holding section 48 (refer to FIGS. 8A and 8B).

Although it may be configured such that the inner wall section 52 is in contact with the outer wall of the peripheral section 14 of the elastic valve body 3 in the state in which the elastic valve body 3 is held by the holding section 48 so that the maximum inner diameter X3 of the inner wall section 52 and the maximum outer diameter X1 of the elastic valve body 3 become equal as illustrated in FIG. 8B, it is preferable to configure the maximum inner diameter X3 of the inner wall section 52 to be larger than the maximum outer diameter X1 of the elastic valve body 3 in the state in which the elastic valve body 3 is held by the holding section 48.

As above, the gap 55 in the housing space 51 is preferably provided on the outer side in the radial direction A with respect to the peripheral section 14 as illustrated in FIG. 8A, but more preferably, is provided also on the outer side in the thickness direction B with respect to the peripheral section 14 of the elastic valve body 3 in addition to the above-described position from a point of view of suppressing the slack of the central section 13 on the bottom face 11 side.

It is because a part of the elastic valve body 3 is pushed from the position of the constricted section 12 to the peripheral section 14 side when the elastic valve body 3 is held by the holding section 48, and the part pushed to the peripheral section 14 side may influence on an increase in thickness of the peripheral section 14 in the thickness direction B as well as an increase in outer diameter of the peripheral section 14 in the radial direction A. Accordingly, the elastic valve body 3 is preferably configured such that, a length T1 of the peripheral section 14 in the thickness direction B in the state in which the elastic valve body 3 is not held by the holding section 48 is shorter than a length T2 (length in the thickness direction B which is sandwiched between the top-face-side coupling section 53 of the top face cap 7 indicated by a solid line and the bottom-face-side coupling section 54 of the bottom face cap 8 indicated by a broken line in FIGS. 10A and 10B) of the housing space 51 in the thickness direction B in the state in which the elastic valve body 3 is held by the holding section 48 as illustrated in FIGS. 10A and 10B, for example.

Here, the "length of the peripheral section in the thickness direction in the state in which the elastic valve body is not held by the holding section" means an extending length of the peripheral section in the thickness direction in the state in which the elastic valve body is not held by the holding section. As illustrated in FIG. 10A, the above-described length indicates an extending length of the peripheral section in the thickness direction B which is sandwiched between the peripheral edge flat part 21 of the peripheral section top face region 17 and the peripheral edge flat part 31 of the peripheral section bottom face region 27 in the state in which the elastic valve body 3 is not held by the holding section 48 in the present embodiment.

In addition, the "length of the housing space in the thickness direction in the state in which the elastic valve body is held by the holding section" means a space width of the housing space in the thickness direction in the state in which the elastic valve body is held by the holding section. As illustrated in FIG. 10A, the above-described length indicates a space width of the housing space in the thickness direction B which is sandwiched between the top-face-side coupling section 53 and the bottom-face-side coupling section 54 in the state in which the elastic valve body 3 is held by the holding section 48 in the present embodiment. More specifically, the above-described length indicates a space width of the housing space in the thickness direction B that is defined by a point of the top-face-side coupling section 53 positioned closest to the side of the reverse direction D of the insertion direction C of the male connector 100 and a point of the bottom-face-side coupling section 54 positioned closest to the side of the insertion direction C.

Figure 10A:
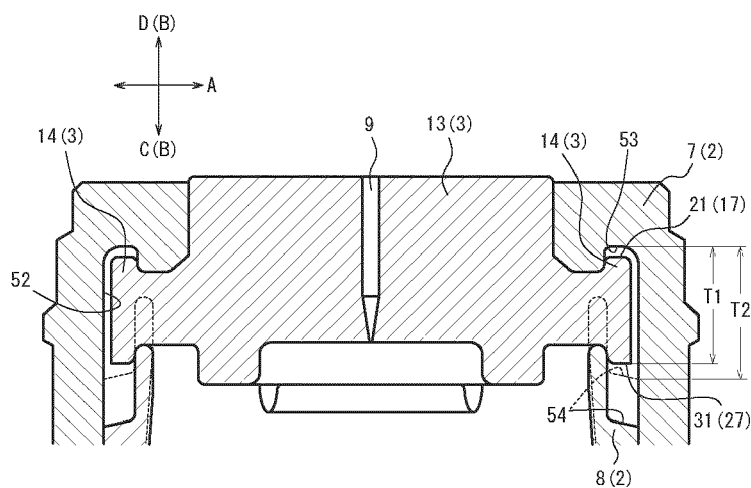
FIG. 10A is a sectional view illustrating a state before an elastic valve body, which has a different shape from the elastic valve body illustrated in FIGS. 8A and 8B, is held by the holding section.
Figure 10B:
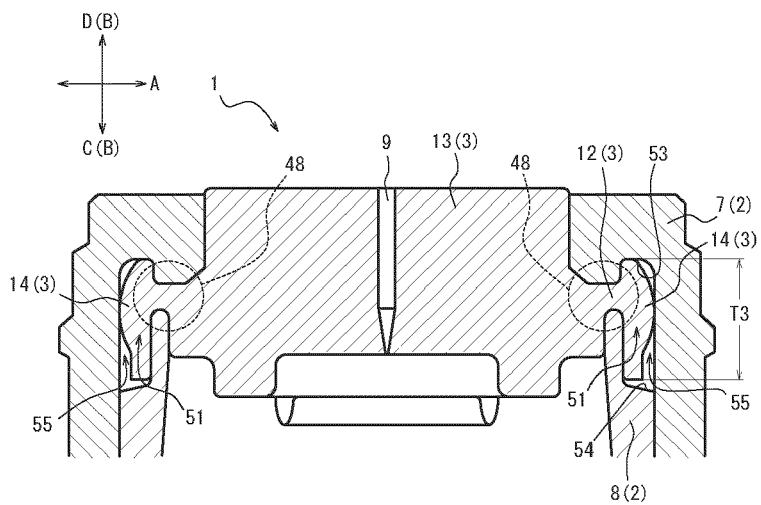
FIG. 10B is a sectional view illustrating a state in which the same elastic valve body is held by the holding section.

When the above-described relationship of T1<T2 is provided, the thickness of the peripheral section 14 of the elastic valve body 3 can be increased in the thickness direction B when the state illustrated in FIG. 10A is changed to the state of FIG. 10B in which the elastic valve body 3 is held and compressed by the holding section 48. In other words, it is possible to set a length T3 (refer to FIG. 10B) of the peripheral section 14 in the thickness direction B in the state in which the elastic valve body 3 is held by the holding section 48 to be longer than the length T1 thereof in the state in which the elastic valve body 3 is not held by the holding section 48.

It may be configured such that the thickness of the peripheral section 14 of the elastic valve body 3 can be increased in the thickness direction B when the elastic valve body 3 is changed from the state of not being held by the holding section 48 (for example, the state illustrated in FIG. 10A) to the state of being held by the holding section 48 (for example, the state illustrated in FIG. 10B), and it may be configured such that the peripheral section 14 of the elastic valve body 3 is in contact with the entire region of the top-face-side coupling section 53 and/or the entire region of the bottom-face-side coupling section 54 in a state in which the elastic valve body 3 is held by the holding section 48.

However, it is preferable to provide the configuration in which the gap is still provided between the peripheral section 14 and the top-face-side coupling section 53 and/or the bottom-face-side coupling section 54 in the state in which the elastic valve body 3 is held by the holding section 48 as illustrated in FIGS. 10A and 10B. In this manner, the peripheral section 14 of the elastic valve body 3 is prevented from receiving the reaction force by the top-face-side coupling section 53 and/or the bottom-face-side coupling section 54, and the slack is hardly formed on the central section 13 on the bottom face 11 side.

Figure 11:
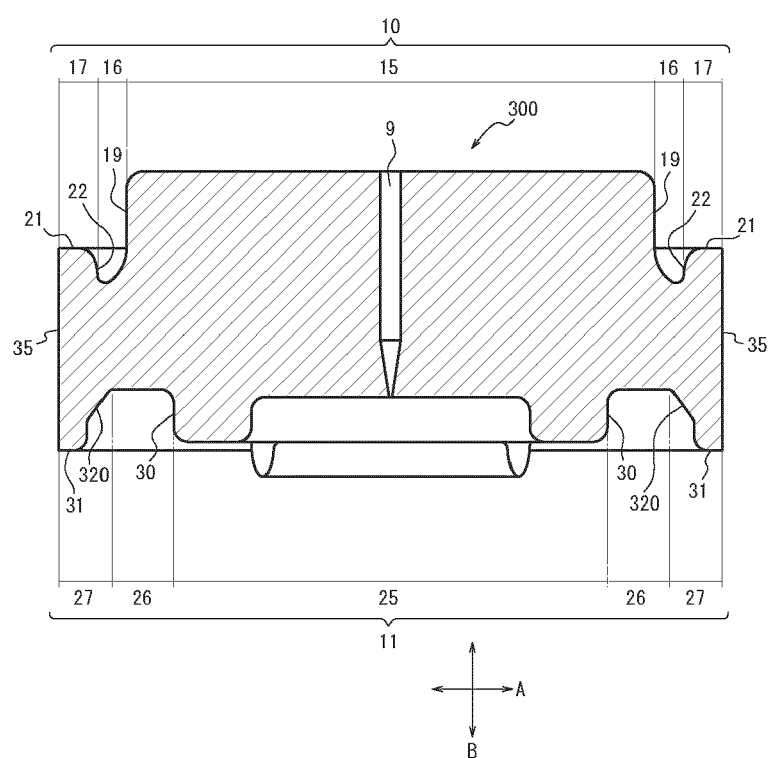
FIG. 11 is a sectional view illustrating an elastic valve body which has a different shape from the elastic valve body illustrated in FIGS. 8A and 8B among elastic valve bodies that can be applied to the present invention.

Further, it is possible to employ an elastic valve body 300 as illustrated in FIG. 11 instead of the elastic valve body 3 according to the present embodiment. As illustrated in FIG. 11, the elastic valve body 300 is configured such that the side wall section 22 in the peripheral section top face region 17 has an inner diameter in the radial direction A gradually decreasing as approaching the bottom face 11 side in the thickness direction B, which is perpendicular to the peripheral edge flat part 21 of the peripheral section top face region 17 (the insertion direction C of the male connector in the state of being fixed inside the connector 1), and further a side wall section 320 of the peripheral section bottom face region 27 has an inner diameter in the radial direction A gradually decreasing as approaching the top face 10 side in the thickness direction B which is perpendicular to the peripheral edge flat part 31 of the peripheral section bottom face region 27 (the reverse direction D of the insertion direction C of the male connector in the state of being fixed inside the connector 1). When the above-described elastic valve body 300 is employed, the engaging projection 41 of the top face cap 7 is guided by the side wall section 22 so as to press the side wall section 19 inward in the radial direction A at the time of assembling the elastic valve body 300, the top face cap 7, and the bottom face cap 8, and thus, a face, on the insertion port 4 side, of the engaging projection 41 of the top face cap 7 and the side wall section 19 of the elastic valve body 300 are brought into intimate contact with each other. In addition, the engaging projection 45 of the bottom face cap 8 is guided by the side wall section 320 so as to press the side wall section 30 inward in the radial direction A, and thus, a face, on the insertion port 4 side, of the engaging projection 45 of the bottom face cap 8 and the side wall section 30 of the elastic valve body 3 are brought into intimate contact with each other (refer to FIG. 6 and the like).

When each face, on the insertion port 4 side, of the engaging projections 41 and 45 is brought into intimate contact with an outer wall of the elastic valve body 300 in this manner, it is possible to cause a part of the elastic valve body 300, which is pushed from the position of the constricted section 12, to be easily moved to the peripheral section 14 side, which is on the outer side in the radial direction A, at the time of compressing the elastic valve body 300 using the holding section 48, and as a result, it is possible to further suppress the slack, on the bottom face 11 side, of the central section 13 of the elastic valve body 300.

In addition, the inner wall section 52, the top-face-side holding section 49, and the top-face-side coupling section 53 form a part of the inner wall of the top face cap 7, and the bottom-face-side holding section 50 and the bottom-face-side coupling section 54 form a part of the outer wall of the bottom face cap 8 in the present embodiment, but the present invention is not limited to the configuration of the present embodiment in which the housing space 51 is defined only by two members of the top face cap 7 and the bottom face cap 8, and, for example, the inner wall section 52 may be configured using the bottom face cap 8 or another member. In addition, the inner wall section 52, the top-face-side holding section 49, the bottom-face-side holding section 50, the top-face-side coupling section 53, and the bottom-face-side coupling section 54 may be configured by combining three or more members, for example.

[Connector 1 in State in which Male Connector 100 is Inserted]

The connector 1 in the state in which the male connector 100 is not inserted has been mainly described hereinabove. Hereinbelow, a description will be given regarding each member of the connector 1 at the time of inserting the male connector insert.

FIG. 12 illustrates the state in which the male connector 100 is inserted into the connector 1. Although FIG. 12 illustrates a configuration of employing the above-described holder 60 instead of the holder 6, the holder 6 may be employed. The same configuration of the connector 1 described above is applied regarding the elastic valve body 3, the top face cap 7, and the bottom face cap 8.

When the male connector 100 is inserted into the connector 1, the tip 101 of the male connector 100 is elastically deformed so as to push the elastic valve body 3 inside the connector 1, and reaches the inside or the vicinity of the liquid flow path 64 in the holder main body 61 through the penetrating slit 9.

The elastic valve body 3 is elastically deformed by insertion of the male connector 100, enters a portion between the inner wall of the bottom face cap 8 and the outer wall of the male connector 100, and is turned into the state of being in intimate contact with the outer surface of the male connector 100. Accordingly, the leakage of the liquid from the connector 1 to the outside is suppressed.

The tip 101 of the male connector 100 abuts against a positioning section 65 formed on an upper face of the holder main body 61 in the state of causing the elastic valve body 3 to be sandwiched therebetween, and is positioned in the insertion direction C of the male connector 100. Although the state is formed in which the elastic valve body 3 is sandwiched between the outer surface of the male connector 100 and the inner wall of the bottom face cap 8, the penetrating slit 9 is provided in the elastic valve body 3, and thus, the liquid flow path inside the male connector 100 is turned into the state of communicating with the liquid flow path 64 through the slit 9.

[Infusion Set 80 Provided with Connector 1]

Finally, a description will be given regarding an infusion set 80 provided with the connector 1 as an embodiment of the present invention with reference to FIG. 13. Herein, the description will be given regarding the infusion set 80 provided with the connector 1 which employs the above-described holder 60, but a shape of the holder can be suitably changed according to a use application or the like of the infusion set, and it is also possible to configure an infusion set provided with a connector that includes the holder 6 or the holder 600 described above.

As illustrated in FIG. 13, the infusion set 80 is provided with a bottle needle 81 which is inserted into an infusion bag housing a liquid, a first tube 82 which is connected to a base of the bottle needle 81 and forms a liquid flow path, a drip infusion cylinder 83 which is connected to the first tube 82 on the liquid flow path downstream side, a second tube 84 which is connected to the drip infusion cylinder 83 and forms a liquid flow path of a liquid to be discharged from the drip infusion cylinder 83, a roller clamp 85 which is attached to an outer peripheral face of the second tube 84 and can adjust the flow amount of a liquid passing through the second tube 84, the connector 1 provided with the holder 60 including a first tube connection port 62, which is connected to an end of the second tube 84 positioned on the liquid flow path downstream side than an installation position of the roller clamp 85, a third tube 86 which is connected to the second tube connection port 63 of the connector 1 and forms the liquid flow path, and a lock connector 87 which is connected to a downstream end of the liquid flow path of the third tube 86.

The infusion set 80 is configured such that the third tube 86 connects the connector 1 and the lock connector 87, but may be configured such that another connector 1 is added between the connector 1 and the lock connector 87, and a tube for connection is also added. In addition, the roller clamp 85 can also be increased in number or arranged at a different position, constituent elements of the infusion set 80 and positions of the constituent elements can be suitably changed and combined by a person in the related art according to a use application of a user, and are not limited to the configuration of the infusion set 80.

In addition, it is preferable to connect the first to third tubes 82, 84 and 86 and the respective constituent elements connected to these tubes using the lock connector.

The infusion set 80 is provided with the connector 1, and thus, can supply a liquid, different from the liquid supplied form the infusion bag to which the bottle needle 81 is connected, to an infusion line through the connector 1, and it is unnecessary to provide different infusion lines for each liquid that needs to be supplied inside a body.

The present invention is not limited to the configuration specified by the above-described embodiment, and various modifications can be made within a scope not departing from a gist of the invention to be described in the claims.

The "top face" of the elastic valve body 3 used herein means a face which has at least a part being exposed to the outside in the state in which the elastic valve body 3 is assembled inside the connector 1, and the "top face cap" means the cap which is in contact with the "top face" of the elastic valve body 3. In the same manner, the "bottom face cap" means the cap which is in contact with the bottom face of the elastic valve body 3.

The present invention relates to a connector and an infusion set, and particularly to a connector that is capable of connecting thereto a male connector such as various medical devices and an infusion set provided with the connector.

REFERENCE NUMERAL LIST 1, 110, 120, 130 connector
2 housing
3, 300 elastic valve body
4 insertion port
5 cap
6, 60, 600 holder
7, 700 top face cap
8 bottom face cap
9 slit
10 top face
11 bottom face
12 constricted section
13 central section
14 peripheral section
15 central top face region
16 constricted section top face region
17 peripheral section top face region
18 central flat face of central top face region
19 side wall section of central top face region
20 curved face of central top face region
21 peripheral edge flat part of peripheral section top face region
22 side wall section of peripheral section top face region
23 top face annular groove
24 groove bottom of top face annular groove
25 central section bottom face region
26 constricted section bottom face region
27 peripheral section bottom face region
28 central flat face of central section bottom face region
29 central projection of central section bottom face region
30 side wall section of central section bottom face region
31 peripheral edge flat part of peripheral section bottom face region
32, 320 side wall section of peripheral section bottom face region
33 bottom face annular groove
34 groove bottom of bottom face annular groove
35 side wall section
36 hollow barrel of top face cap
37 flange of top face cap
38 extending section
39 edge
40 screw thread
41 engaging projection of top face cap
42 inner wall
43 hollow barrel of bottom face cap
44 flange of bottom face cap
45 engaging projection of bottom face cap
46 outer cylindrical section
47 male luer section
48 holding section
49 top-face-side holding section
50 bottom-face-side holding section
51 housing space 52, 520 inner wall section
53 top-face-side coupling section
54 bottom-face-side coupling section
55 gap
61 holder main body
62 upstream port
63 downstream port
64 liquid flow path
65 positioning section
70 hollow section
71 hollow section of holder
80 infusion set
81 bottle needle
82 first tube
83 drip infusion cylinder
84 second tube
85 roller clamp
86 third tube
87 lock connector
100 male connector
101 tip
200 connector
202 housing
203 elastic valve body
204 insertion port
207 top face cap
208 bottom face cap
211 bottom face
212 constricted section
213 central section
214 peripheral section
245 engaging projection of bottom face cap
248 holding section
251 housing space
601 cock
602 holder main body
603 upstream port
604 downstream port
605 branch port
606 liquid flow path
A radial direction of elastic valve body
B thickness direction of elastic valve body
C male connector insertion direction
D reverse direction of male connector insertion direction
E circumferential direction of elastic valve body
L length of curved face of elliptical top face flat part in major-axis direction
P point of top-face-side holding section which is positioned on outermost side in radial direction
Q point of bottom-face-side holding section which is positioned on outermost side in radial direction
T1 length of peripheral section in thickness direction in state in which elastic valve body is not held by holding section
T2 length of housing space in thickness direction in state in which elastic valve body is held by holding section
T3 length of peripheral section in thickness direction in state in which elastic valve body is held by holding section
V1 volume of peripheral section in state in which elastic valve body is held by holding section
V2 volume of peripheral section in state in which elastic valve body is not held by holding section
V3 volume of housing space in state in which elastic valve body is held by holding section
X1 maximum outer diameter of elastic valve body in state in which elastic valve body is held by holding section
X2 maximum outer diameter of elastic valve body in state in which elastic valve body is not held by holding section
X3 maximum inner diameter of inner wall section

The invention claimed is:

1. A connector comprising:
an elastic valve body that includes a top face on which a slit is formed and a bottom face opposite the top face, the elastic valve body comprising a constricted section, and a peripheral section located radially outward of the constricted section; and
a housing comprising a top face cap comprising a first engaging projection that projects downward and contacts the top face of the elastic valve body at the constricted section, a bottom face cap comprising a second engaging projection that projects upward and contacts the bottom face of the elastic valve body at the constricted section, such the first engaging projection and the second engaging projection compress and hold the constricted section of the elastic valve body;
wherein the constricted section of the elastic valve body has, in a direction perpendicular to a radial direction, a first thickness in a first state in which the first engaging projection and the second engaging projection do not compress and hold the constricted section and a second thickness in a second state in which the first engaging projection and the second engaging projection compress and hold the constricted section, wherein a ratio of the second thickness to the first thickness is in a range of 0.2:1 to 0.3:1,
wherein the elastic valve body and the housing are configured such that, in a radial direction along the constricted section, an outer diameter of the elastic valve body in the second state in which the first engaging projection and the second engaging projection compress and hold the constricted section is larger than an outer diameter of the elastic valve body in the first state in which the first engaging projection and the second engaging projection do not compress and hold the constricted section,
wherein the housing includes an inner wall section that surround the peripheral section of the elastic valve body, and
wherein, due to bulging of the elastic valve body caused by compression of the constricted section by the first engaging projection and the second engaging projection, a thickness of the peripheral section of the elastic valve body in a radial direction along the constricted section is greater than a thickness of the peripheral section of the elastic valve body in a radial direction along a top face side of the peripheral section and greater than a thickness of the peripheral section of the elastic valve body in a radial direction along a bottom face side of the peripheral section, such that a gap is located between the top face side of the peripheral section and the inner wall section, and a gap is formed between the bottom face side of the peripheral section and the inner wall section.

2. The connector according to claim 1, wherein the elastic valve body has a substantially circular outer shape.

3. The connector according to claim 2, wherein an inner diameter of the inner wall section is at a maximum at a position radially outward of the constricted section.

4. The connector according to claim 2, wherein:
the peripheral section is housed in a housing space that is defined by the inner wall section, the first engaging projection, the second engaging projection, a top-face-side coupling section that connects an end of the inner wall section and the first engaging projection, and a bottom-face-side coupling section that connects another end of the inner wall section and the second engaging projection, and the peripheral section is in contact with (i) the top-face-side coupling section, and/or (ii) the bottom-face-side coupling section.

5. The connector according to claim 1, wherein, in a radial direction along the constricted section, the peripheral section and the inner wall section are in contact with each other in the second state in which the elastic valve body is compressed and held by the first engaging projection and the second engaging projection.

6. The connector according to claim 5, wherein an inner diameter of the inner wall section is at a maximum at a position radially outward of the constricted section.

7. The connector according to claim 5, wherein:

the peripheral section is housed in a housing space that is defined by the inner wall section, the first engaging projection, the second engaging projection, a top-face-side coupling section that connects an end of the inner wall section and the first engaging projection, and a bottom-face-side coupling section that connects another end of the inner wall section and the second engaging projection, and the peripheral section is in contact with (i) the top-face-side coupling section, and/or (ii) the bottom-face-side coupling section.

8. The connector according to claim 1, wherein the elastic valve body and the housing are configured such that a maximum inner diameter of the inner wall section is larger than a maximum outer diameter of the elastic valve body in the first state in which the first engaging projection and the second engaging projection do not compress and hold the constricted section.

9. The connector according to claim 8, wherein the elastic valve body and the housing are configured such that the maximum inner diameter of the inner wall section is larger than a maximum outer diameter of the elastic valve body in the second state in which the first engaging projection and the second engaging projection compress and hold the constricted section.

10. The connector according to claim 8, wherein the elastic valve body and the housing are configured such that the inner wall section is in contact with an outer wall of the elastic valve body in the second state in which the elastic valve body is compressed and held by the first engaging projection and the second engaging projection.

11. An infusion set comprising the connector according to claim 1.

12. An infusion set comprising the connector according to claim 8.

* * * * *